(12) United States Patent
Nakano

(10) Patent No.: US 8,768,442 B2
(45) Date of Patent: Jul. 1, 2014

(54) WAKEFUL-STATE DATA GENERATING APPARATUS AND WAKEFULNESS DEGREE DETERMINING APPARATUS

(75) Inventor: Yasuhiko Nakano, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 357 days.

(21) Appl. No.: 13/343,375

(22) Filed: Jan. 4, 2012

(65) Prior Publication Data

US 2012/0197091 A1     Aug. 2, 2012

(30) Foreign Application Priority Data

Jan. 27, 2011   (JP) .................................. 2011-015485

(51) Int. Cl.
*A61B 5/04*          (2006.01)
(52) U.S. Cl.
USPC ........................................................... 600/513
(58) Field of Classification Search
USPC .................................... 600/509, 513, 519–20
See application file for complete search history.

(56) References Cited

U.S. PATENT DOCUMENTS

2009/0275847 A1   11/2009  Karasudani

FOREIGN PATENT DOCUMENTS

WO     WO2008/65724    6/2008

*Primary Examiner* — Amanda Patton
(74) *Attorney, Agent, or Firm* — Staas & Halsey LLP

(57) ABSTRACT

A wakeful-state data generating apparatus includes at least one processor and at least one storage device, the at least one storage device configured to; store a first correlation between value of variation in heartbeat interval and maximum spectral density, and store a second correlation between heartbeat rate and wakeful-state maximum frequency, the at least one processor configured to; calculate a value of variation in heartbeat interval from a heartbeat signal of a subject, estimate a wakeful-state maximum spectral density of the subject, on the basis of the first correlation and the calculated value of variation, calculate a heartbeat rate from the heartbeat signal, estimate a wakeful-state maximum frequency of the subject, on the basis of the second correlation and the calculated heartbeat rate, and generate wakeful-state data including the estimated wakeful-state maximum spectral density and the estimated wakeful-state maximum frequency.

20 Claims, 19 Drawing Sheets

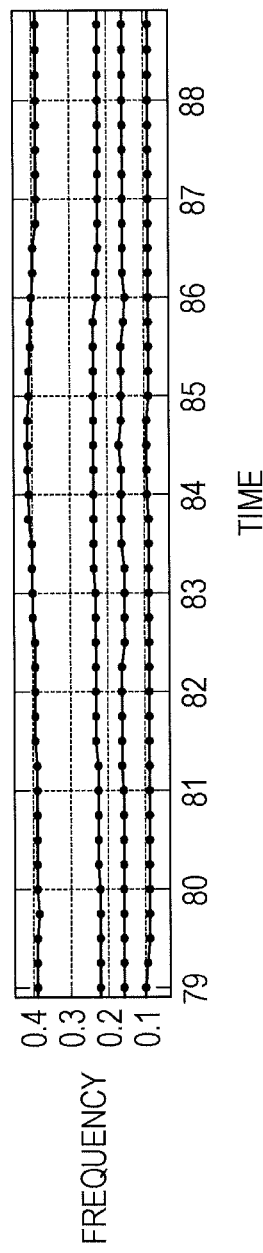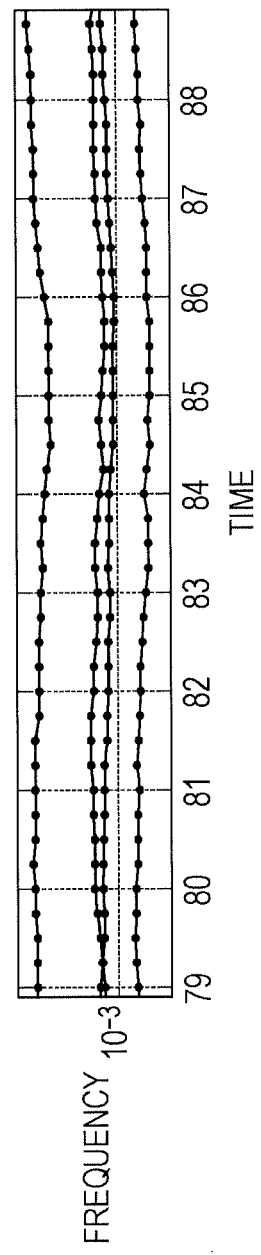

FIG. 24

| AGE (yr) | BASAL METABOLIC RATE (MALE) (kcal/day) | BASAL METABOLIC RATE (FEMALE) (kcal/day) |
|---|---|---|
| 1 TO 2 | 700 | 700 |
| 3 TO 5 | 900 | 860 |
| 6 TO 8 | 1090 | 1000 |
| 9 TO 11 | 1290 | 1180 |
| 12 TO 14 | 1480 | 1340 |
| 15 TO 17 | 1610 | 1300 |
| 18 TO 29 | 1550 | 1210 |
| 30 TO 49 | 1500 | 1170 |
| 50 TO 69 | 1350 | 1110 |
| 70 AND ABOVE | 1220 | 1010 |

| AGE [yr] | RSA VALUE [msec] |
|---|---|
| 20 TO 29 | 45 |
| 30 TO 39 | 40 |
| 40 TO 49 | 35 |
| 50 TO 59 | 30 |
| ⋮ | ⋮ |

WAKEFUL-STATE DATA GENERATING APPARATUS AND WAKEFULNESS DEGREE DETERMINING APPARATUS

CROSS-REFERENCE TO RELATED APPLICATIONS

This application is based upon and claims the benefit of priority of the prior Japanese Patent Application No. 2011-15485, filed on Jan. 27, 2011, the entire contents of which are incorporated herein by reference.

FIELD

The embodiments relate to a wakeful-state data generating apparatus and a wakefulness degree determining apparatus.

BACKGROUND

In related art, there exist techniques which use biological information about the subject to determine the degree of the subject's wakefulness without imposing a burden on the subject. For example, such techniques can be applied to a vehicle to determine the degree of the driver's wakefulness, and notify the driver of impending danger.

For example, there exists related art which determines the degree of the subject's wakefulness by keeping track of changes in maximum frequency and maximum spectral density calculated by frequency analysis from the heartbeat signal of the subject (for example, International Publication Pamphlet No. WO 2008/65724). In related art, wakeful-state data, which indicates the maximum frequency and maximum spectral density in a wakeful state, that is, a state of no sleepiness serves as a reference for the degree of wakefulness. In related art, the maximum frequency and the maximum spectral density are calculated every time the heartbeat signal of the subject is acquired. Then, the degree of the subject's wakefulness is determined in real time on the basis of the amount of change of the calculated values relative to the wakeful-state data.

SUMMARY

According to an aspect of the invention, a wakeful-state data generating apparatus includes at least one processor and at least one storage device, the at least one storage device configured to; store a first correlation between value of variation in heartbeat interval and maximum spectral density, and store a second correlation between heartbeat rate and wakeful-state maximum frequency, the at least one processor configured to; calculate a value of variation in heartbeat interval from a heartbeat signal of a subject, estimate a wakeful-state maximum spectral density of the subject, on the basis of the first correlation and the calculated value of variation, calculate a heartbeat rate from the heartbeat signal, estimate a wakeful-state maximum frequency of the subject, on the basis of the second correlation and the calculated heartbeat rate, and generate wakeful-state data including the estimated wakeful-state maximum spectral density and the estimated wakeful-state maximum frequency.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 19 is a diagram illustrating maximum frequency in a times series;

FIG. 20 is a diagram illustrating maximum spectral density in a times series;

FIG. 24 is a diagram illustrating an example of a table describing basal metabolic rate by age;

DESCRIPTION OF EMBODIMENTS

In the related art, it is difficult to generate wakeful-state data.

For example, in related art, frequency analysis is executed in the course of generating wakeful-state data. This frequency analysis uses several minutes of heartbeat signal in order to generate stable wakeful-state data. Accordingly, when detecting a heartbeat signal, the subject is required to maintain a wakeful state for several minutes. If the subject is unable to maintain a wakeful state for several minutes, accurate wakeful-state data cannot be generated, making it impossible to accurately determine the degree of wakefulness.

Embodiments of the present disclosure disclose a wakeful-state data generating apparatus and a wakefulness degree determining apparatus which can easily generate wakeful-state data.

Hereinbelow, embodiments of a wakeful-state data generating apparatus, a wakeful-state data generating method, a storage medium storing a wakeful-state data generating program, and a wakefulness degree determining apparatus according to the present disclosure are described in detail with reference to the drawings. It should be noted that these embodiments are not intended to limit the present invention. It is possible to combine individual embodiments as appropriate insofar as their contents of processing do not conflict with each other.

Embodiment 1

Figure 1:
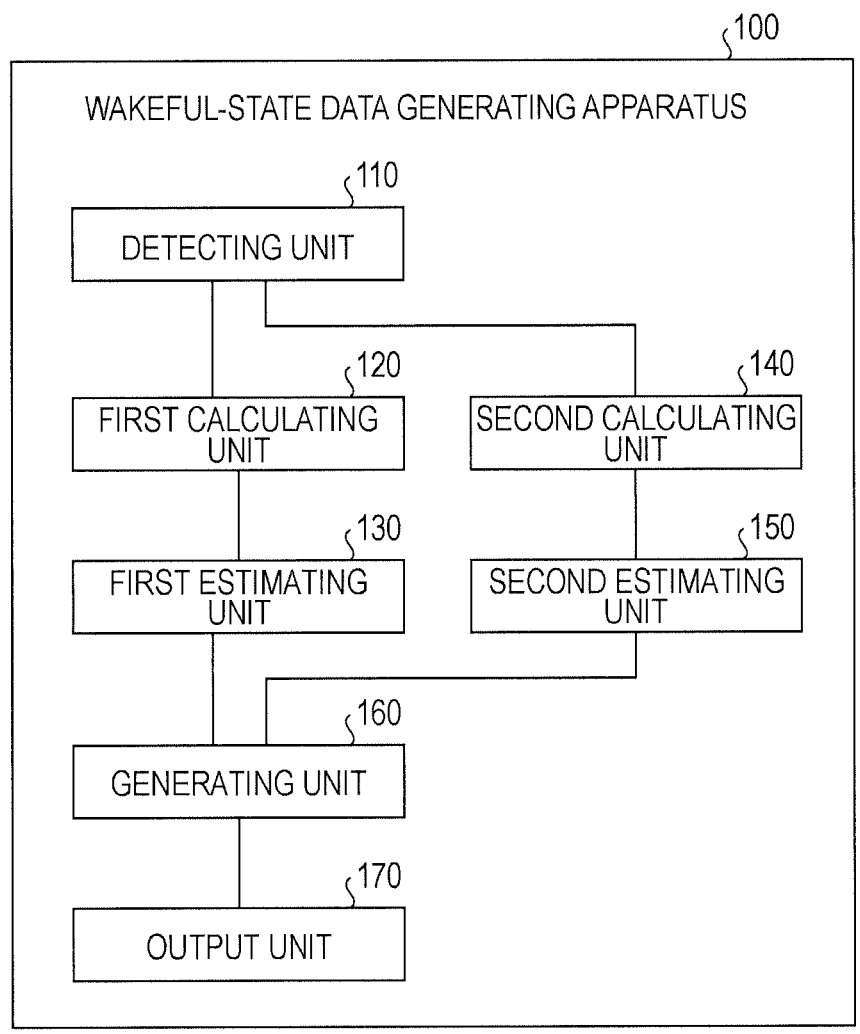
FIG. 1 is a diagram illustrating the functional configuration of a wakeful-state data generating apparatus according to Embodiment 1.

An example of the configuration of a wakeful-state data generating apparatus according to Embodiment 1 is described. FIG. 1 is a diagram illustrating the configuration of the wakeful-state data generating apparatus according to Embodiment 1. As illustrated in FIG. 1, a wakeful-state data generating apparatus 100 has a detecting unit 110, a first calculating unit 120, a first estimating unit 130, a second calculating unit 150, a generating unit 160, and an output unit 170.

The detecting unit 110 detects the heartbeat signal of a subject. For example, the detecting unit 110 applies voltage to electrodes in contact with the subject, and acquires the heartbeat signal of the subject from the potential difference between the electrodes. It should be noted that the electrodes used by the detecting unit 110 correspond to, for example, electrodes embedded in wristwatch-type compact equipment.

Figure 2:
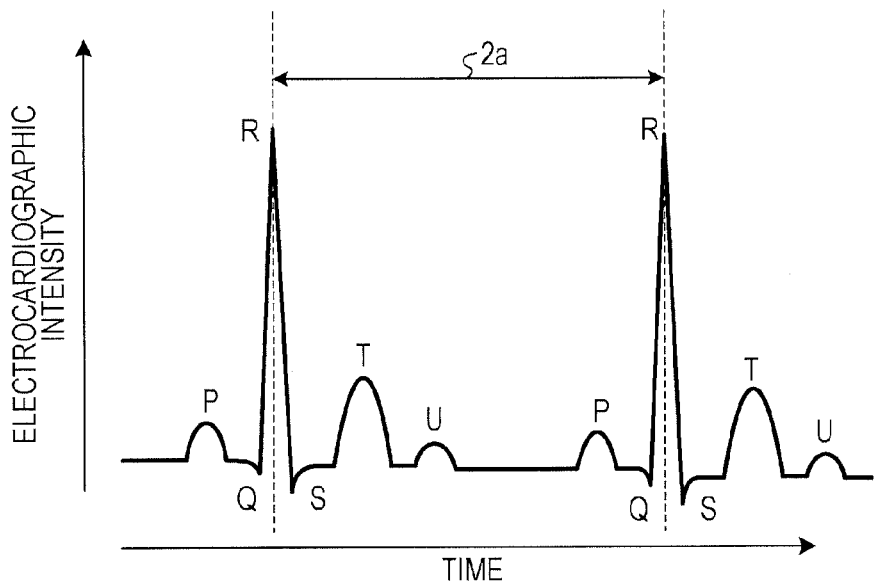
FIG. 2 is a diagram illustrating an example of a heartbeat signal detected by a detecting unit.

FIG. 2 is a diagram illustrating an example of a heartbeat signal detected by the detecting unit. In FIG. 2, the horizontal axis represents elapse of time, and the vertical axis represents electrocardiographic intensity. As illustrated in FIG. 2, the electrocardiographic signal of a healthy person generally has four waveforms, which are called a P wave, a QRS wave, a T wave, and a U wave in time series order. In particular, the QRS wave is detected as an acute peak, and includes a Q wave as the onset point of the peak, an R wave as the apex of the peak, and an S wave as the offset point of the peak. One cycle of the waveforms from the P wave to the U wave corresponds to one heartbeat. An R-R Interval (RRI) 2a calculated as the interval between an R wave and the next R wave corresponds to a heartbeat interval indicating the time interval between heartbeats. The detecting unit 110 outputs data of the detected heartbeat signal as heartbeat signal data to the first calculating unit 120 and the second calculating unit 140.

The first calculating unit 120 calculates the value of variation in heartbeat interval from the subject's heartbeat signal. Then, the first calculating unit 120 outputs the calculated value of variation in heartbeat interval to the first estimating unit 130. Hereinbelow, processing in the first calculating unit 120 is described in detail.

Figure 3:
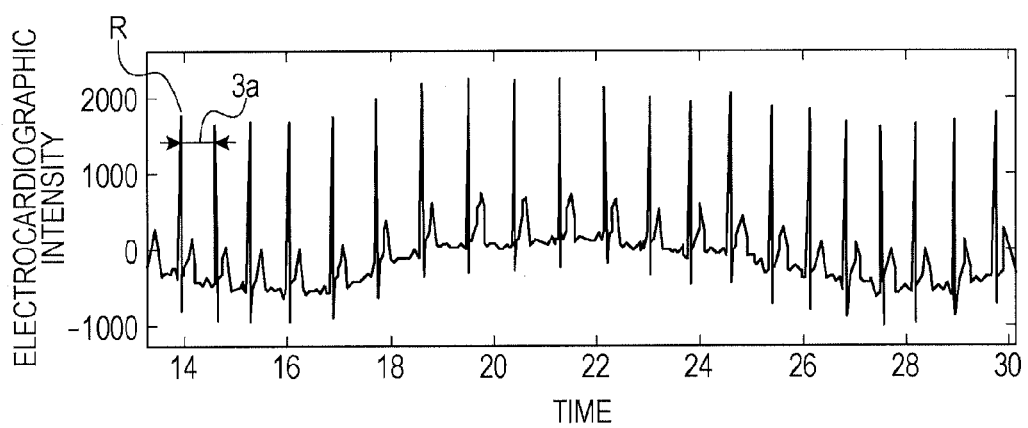
FIG. 3 is a diagram for explaining a process of calculating a heartbeat interval.

For example, the first calculating unit 120 calculates a heartbeat interval from the heartbeat signal data inputted from the detecting unit 110. FIG. 3 is a diagram for explaining a process of calculating a heartbeat interval. In FIG. 3, the horizontal axis represents elapse of time, and the vertical axis represents electrocardiographic intensity. As illustrated in FIG. 3, as R waves, the first calculating unit 120 detects amplitude peaks at which the amplitude of the heartbeat signal becomes equal to or greater than a threshold. Then, upon each detection of an R wave, the first calculating unit 120 calculates a heartbeat interval 3a from the appearance times of the detected R waves. It should be noted that the method of detecting amplitude peaks is not limited to the above-mentioned method. For example, the first calculating unit 120 may employ a method such as using zero-crossings at which the differential coefficient of the heartbeat signal changes from positive to negative, or detecting amplitude peaks by performing pattern matching.

Figure 4:
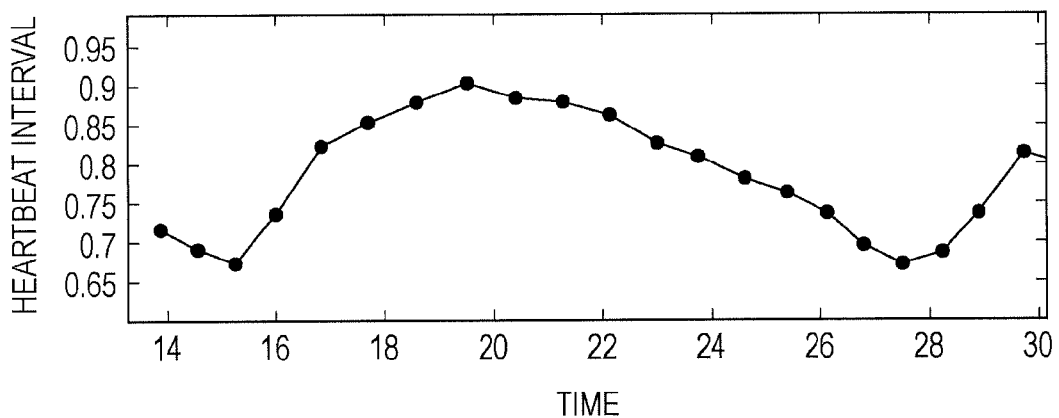
FIG. 4 is a diagram illustrating an example of heartbeat interval data.

For example, the first calculating unit 120 generates heartbeat interval data indicating variation of the calculated heartbeat interval with elapse of time. FIG. 4 is a diagram illustrating an example of heartbeat interval data. In FIG. 4, the horizontal axis represents elapse of time, and the vertical axis represents heartbeat interval. As illustrated in FIG. 4, for example, the first calculating unit 120 generates heartbeat interval data by associating the calculated heartbeat interval with the detection time of each R wave.

For example, the first calculating unit 120 calculates the value of variation in heartbeat interval from the generated heartbeat interval data. It should be noted that the value of variation in heartbeat interval calculated by the first calculating unit 120 corresponds to, for example, a respiratory sinus arrhythmia value. Hereinafter, respiratory sinus arrhythmia is referred to as RSA.

Figure 5:
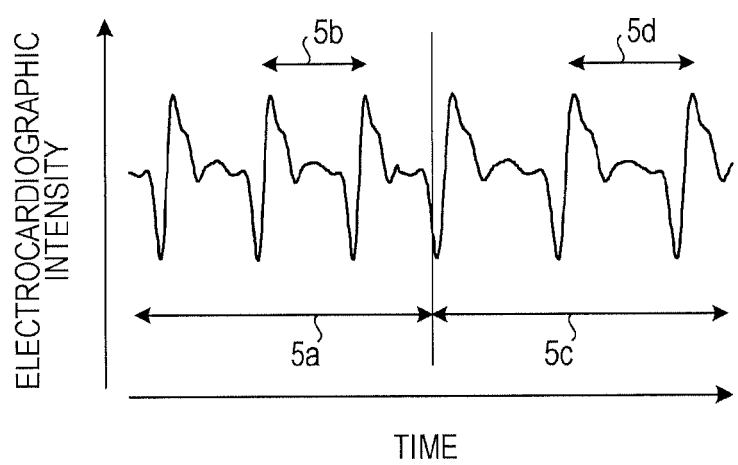
FIG. 5 is a diagram for explaining respiratory sinus arrhythmia.

Referring to FIGS. 5 to 9, RSA and RSA value is described. FIG. 5 is a diagram for explaining respiratory sinus arrhythmia. In FIG. 5, the horizontal axis represents elapse of time, and the vertical axis represents electrocardiographic intensity. RSA is a physiological arrhythmia in which the heartbeats become faster during inspiration and become slower during expiration. That is, as illustrated in FIG. 5, RSA is detected as such variation of heartbeat interval that the heartbeat interval is shortened to a heartbeat interval 5b during inspiration 5a, and the heartbeat rate is prolonged to a heartbeat interval 5d during expiration 5c. The difference between the heartbeat interval 5d and the heartbeat interval 5b indicates the RSA value, which serves as an index for quantitatively evaluating the degree of RSA.

Figure 6:
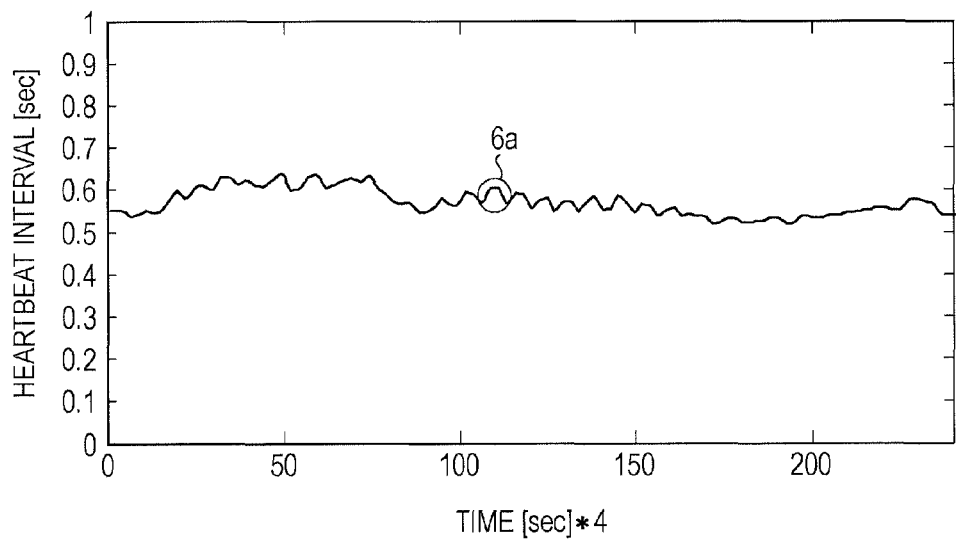
FIG. 6 is a diagram for explaining RSA value.
Figure 7:
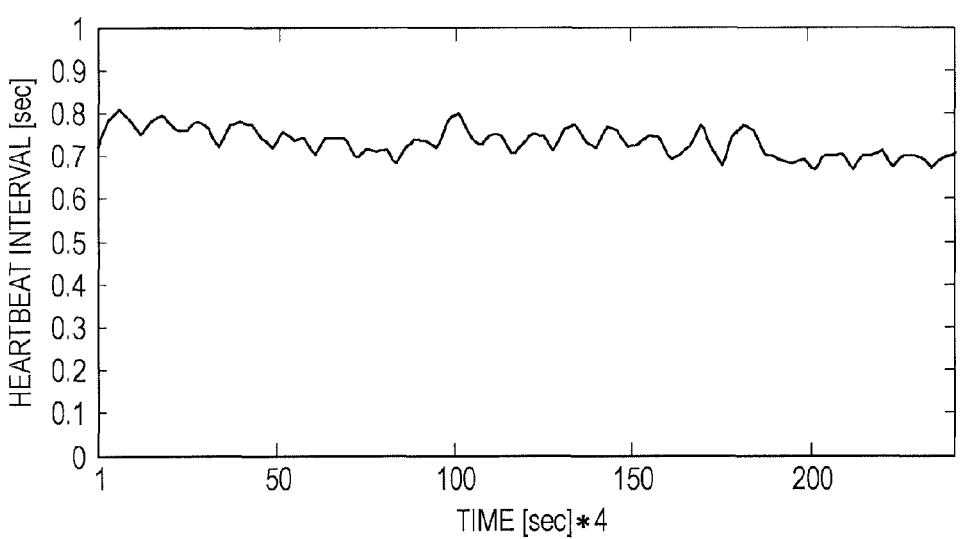
FIG. 7 is a diagram for explaining RSA value.
Figure 8:
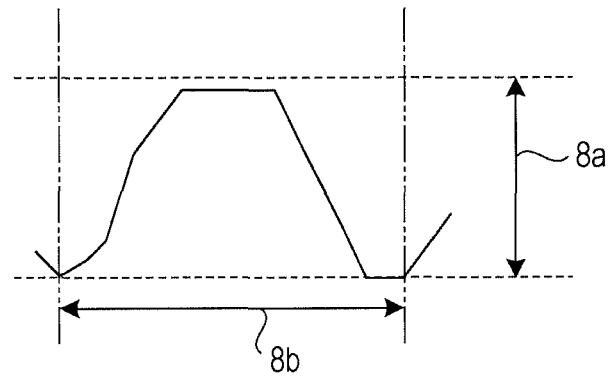
FIG. 8 is a diagram for explaining RSA value.

It is known that the RSA value changes between wakeful and non-wakeful states. FIGS. 6 to 8 are diagrams for explaining RSA value. In FIGS. 6 to 8, the horizontal axis represents elapse of time [sec]*4, and the vertical axis represents heartbeat interval [sec]. FIG. 6 illustrates an example of heartbeat interval data in a state of no sleepiness, that is, during wakefulness, and FIG. 7 illustrates an example of heartbeat interval data in a state of increased sleepiness, that is, during non-wakefulness. FIG. 8 is an enlarged view of a waveform 6a illustrated in FIG. 6. The peak value of each waveform corresponds to the heartbeat interval during expiration, and its smallest value corresponds to the heartbeat interval during inspiration. That is, an amplitude 8a of each waveform corresponds to the RSA value. Also, a wavelength 8b of each waveform corresponds to one respiratory period. As illustrated in FIGS. 6 and 7, when the state of the subject changes from wakefulness to non-wakefulness, the RSA value of each waveform becomes larger.

Figure 9:
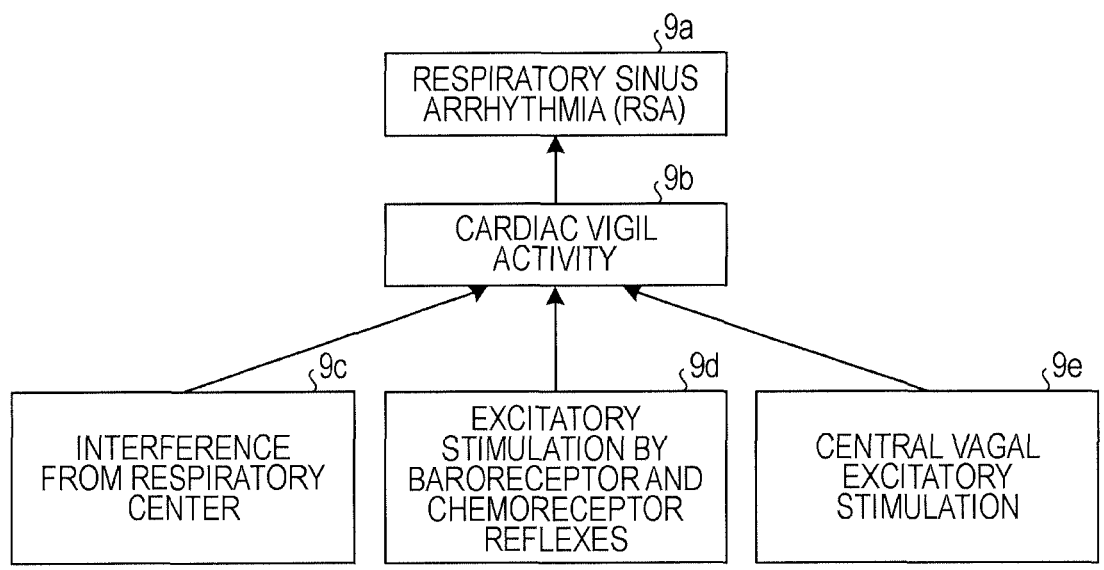
FIG. 9 is a diagram for explaining the physiological mechanism of respiratory sinus arrhythmia.

The change in RSA value occurs owing to control by various physiological mechanisms as disclosed in Hayano Junichiro, "Aging alteration of biological rhythm", 95CLINI- CIAN, 94 No. 429, or the like. FIG. 9 is a diagram for explaining the physiological mechanism of respiratory sinus arrhythmia. As illustrated in FIG. 9, RSA 9a appears in accordance with the activity level of a cardiac vagal activity 9b. The activity level of the cardiac vagal activity 9b is subject to the following three kinds of control: interference from the respiratory center 9c, excitatory stimulation by baroreceptor and chemoreceptor reflexes 9d, and central vagal excitatory stimulation 9e. Among these, the interference from the respiratory center 9c includes inhibitory stimulation during inspiration and excitatory stimulation during expiration. During wakefulness, the RSA 9a is relatively insusceptible to control by the excitatory stimulation by baroreceptor and chemoreceptor reflexes 9d and the central vagal excitatory stimulation 9e, and is strongly susceptible only to control by the interference from the respiratory center 9c.

The inventor has focused attention on the fact that variation of RRI with respiration, that is, the value of variation in heartbeat interval (RSA) is affected by the degree of wakefulness of the subject. When a heartbeat signal for the duration of at least one respiration can be acquired, it is possible to calculate the value of variation in heartbeat interval which is strongly affected by the state of wakefulness. Then, by using the value of variation in heartbeat interval, wakeful-state data can be generated by a method described later. The wakeful-state data generated from the value of variation in heartbeat interval is stable wakeful-state data in comparison to wakeful-state data generated from heartbeat data taken for about the same duration of time (about the duration of one respiration). That is, it is considered that even with wakeful-state data generated over a short duration of time, the state of the subject during wakefulness can be estimated with high accuracy.

As illustrated in FIG. 6, the first calculating unit 120 calculates an RSA value from wakeful-state heartbeat interval data, for example. For example, as the smallest value, the first calculating unit 120 acquires the heartbeat interval at the zero-crossing where the differential coefficient of the heartbeat data changes from negative to positive, and as a peak value, the first calculating unit 120 acquires the heartbeat interval at the zero-crossing where the differential coefficient changes from positive to negative. Upon each acquisition of a peak value, the first calculating unit 120 calculates the difference between the acquired peak value and the smallest value acquired immediately previously as the RSA value. It should be noted that the method of calculating an RSA value is not limited to the above-mentioned method. For example, it is also possible to employ a method of detecting each waveform by performing pattern matching, and calculating the amplitude of the detected waveform.

The description now returns to FIG. 1. The first estimating unit 130 estimates the wakeful-state maximum spectral density of the subject from the value of variation calculated by the first calculating unit 120, on the basis of a pre-recorded correlation between value of variation and wakeful-state maximum spectral density. The spectral density in embodiments indicates power spectral density. For example, by using a correlation between wakeful-state RSA value and wakeful-state maximum spectral density, the first estimating unit 130 estimates a wakeful-state maximum spectral density from a wakeful-state RSA value.

Figure 10:
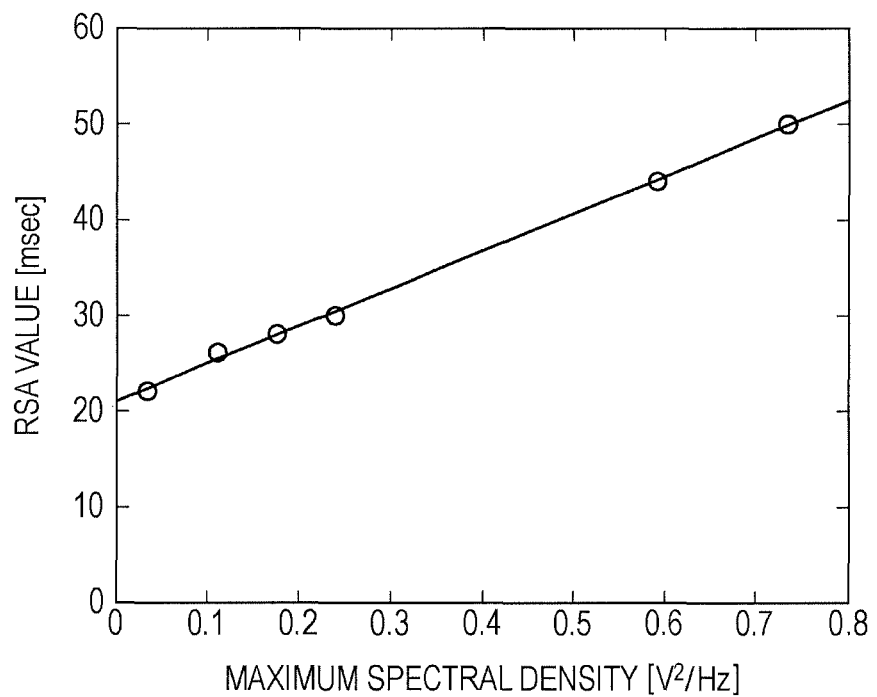
FIG. 10 is a diagram illustrating a correlation between wakeful-state RSA value and wakeful-state maximum spectral density.

Here, the correlation used by the first estimating unit 130 is described. FIG. 10 is a diagram illustrating a correlation between wakeful-state RSA value and wakeful-state maximum spectral density. In FIG. 10, the horizontal axis represents wakeful-state maximum spectral density [$V^2$/Hz], and the vertical axis represents wakeful-state RSA value [msec].

As illustrated in FIG. 10, by actually measuring a wakeful-state RSA value and a wakeful-state maximum spectral density for each subject, and plotting the measurement results, a regression line is obtained. It should be noted that in order to generate a regression line indicating the correlation in advance, heartbeat signals are acquired for a plurality of subjects who are in a wakeful state, and RSA values and maximum spectral densities are calculated from the acquired heartbeat signals. Letting PSD represent maximum spectral density, and RSA represent RSA value, this regression line is expressed as follows:

$$PSD=(RSA-21.0195)/39.2161 \qquad (1)$$

For example, the first estimating unit 130 acquires the wakeful-state RSA value of the subject from the first calculating unit 120. Then, the first estimating unit 130 substitutes the acquired wakeful-state RSA value into Equation (1) mentioned above to calculate a wakeful-state maximum spectral density.

The second calculating unit 140 calculates a heartbeat rate from the heartbeat signal of the subject. For example, the second calculating unit 140 calculates a heartbeat interval from the heartbeat signal data inputted from the detecting unit 110. Since the process in which the second calculating unit 140 calculates a heartbeat interval is the same as the process in which the first calculating unit 120 calculates a heartbeat interval, a description of the process is omitted. The second calculating unit 140 calculates a heartbeat rate [counts/min] by taking the inverse of the calculated heartbeat interval, and converting the result into a value per minute. Then, the second calculating unit 140 outputs the calculated heartbeat rate to the second estimating unit 150.

The second estimating unit 150 estimates the wakeful-state maximum frequency of the subject from the heartbeat rate calculated by the second calculating unit 140, on the basis of a pre-recorded correlation between heartbeat rate and wakeful-state maximum frequency. For example, the second estimating unit 150 calculates a wakeful-state respiration rate from a wakeful-state heartbeat rate, on the basis of a correlation between heartbeat rate and respiration rate. Then, by exploiting the fact that a respiratory period found from a respiration rate corresponds to a maximum frequency, the second estimating unit 150 calculates a wakeful-state maximum frequency from the wakeful-state respiration rate. It should be noted that the maximum frequency is, for example, the frequency at a maximum point obtained by performing frequency analysis of the heartbeat interval data illustrated in FIG. 6. That is, the maximum frequency corresponds to the average value of the wavelengths of the waveforms illustrated in FIG. 6, that is, the respiratory period.

Figure 11:
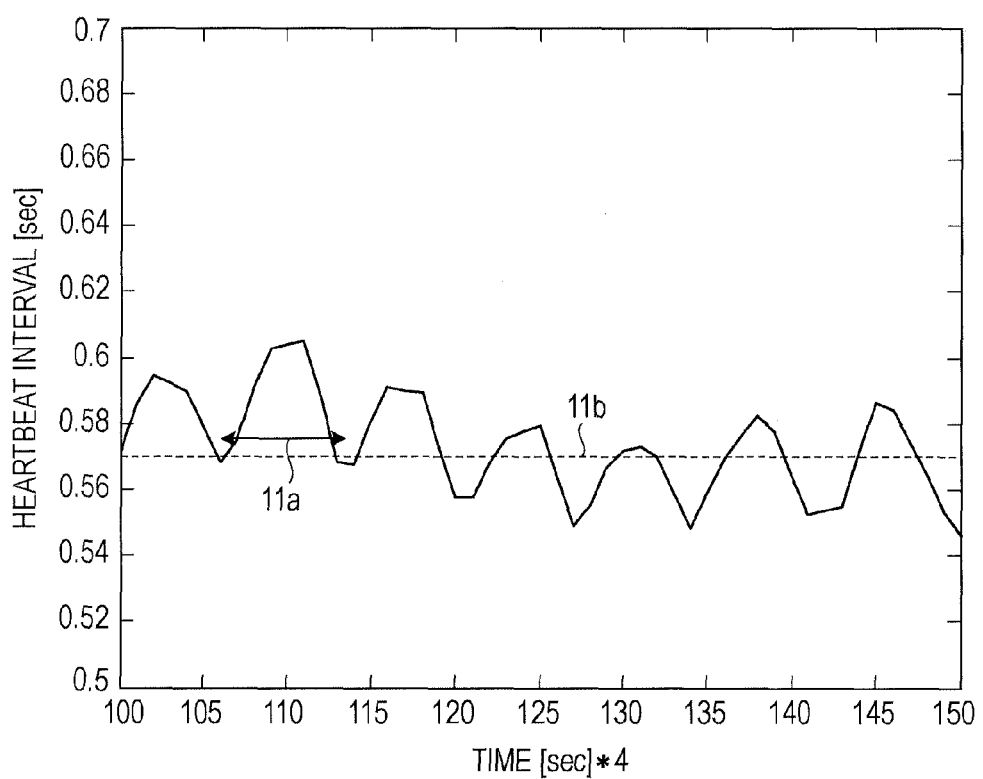
FIG. 11 is a diagram illustrating an example of the method of calculating the ratio between respiratory period and heartbeat period.

Now, the correlation between heartbeat rate and respiration rate which is used by the second estimating unit 150 is described. Letting Bn represent respiration rate [counts/min], and HR represent heartbeat rate [counts/min], this correlation is expression by Equation (2) below:

$$Bn=HR/C \qquad (2)$$

where "C" is a constant, and corresponds to the ratio between respiratory period and heartbeat period in the heartbeat interval data. FIG. 11 is a diagram illustrating an example of the method of calculating the ratio between respiratory period and heartbeat period. In FIG. 11, the horizontal axis represents elapse of time [sec]*4, and the vertical axis represents heartbeat interval [sec]. As illustrated in FIG. 11, the respiratory period corresponds to the average value of a wavelength 11a of each waveform, and the average value calculated using data on a plurality of subjects is approximately 7 [sec]*4, that is, approximately 1.8 [sec]. The heartbeat period corresponds to the average value of heartbeat interval indicated by a baseline 11b, and the average value calculated using data on a plurality of subjects is approximately 0.57 [sec]. That is, by dividing the respiratory period by the heartbeat period, the constant C in Equation (2) is calculated as approximately 3.2. It should be noted that the constant C is not limited to this example but may be set to an arbitrary value by a person who uses the wakeful-state data generating apparatus 100. For example, for an adult person, the average respiration rate is 16 to 18 [counts/min], and the average heartbeat rate is 60 to 70 [counts/min]. Thus, the constant C may be set to an arbitrary value appropriate to each individual subject, within the range of approximately 3 to 4.

For example, the second estimating unit 150 calculates a wakeful-state respiration rate by substituting the heartbeat rate calculated by the second calculating unit 140 into Equation (2) mentioned above. Then, the second estimating unit 150 calculates a wakeful-state maximum frequency by substituting the wakeful-state respiration rate into Equation (3) below:

$$F = Bn/60 \qquad (3)$$

where F denotes wakeful-state maximum frequency.

The generating unit 160 generates wakeful-state data including the wakeful-state maximum spectral density estimated by the first estimating unit 130, and the wakeful-state maximum frequency estimated by the second estimating unit 150. For example, the generating unit 160 acquires a wakeful-state maximum spectral density from the first estimating unit 130, and acquires a wakeful-state maximum frequency from the second estimating unit 150. Then, the generating unit 160 generates wakeful-state data including the acquired wakeful-state maximum spectral density and the acquired wakeful-state maximum frequency. This wakeful-state data serves as a reference in determining the degree of the subject's wakefulness.

The output unit 170 outputs the wakeful-state data generated by the generating unit 160. The output unit 170 is, for example, an interface device. For example, the output unit 170 transmits the wakeful-state data generated by the generating unit 160 to an external device.

Figure 12:
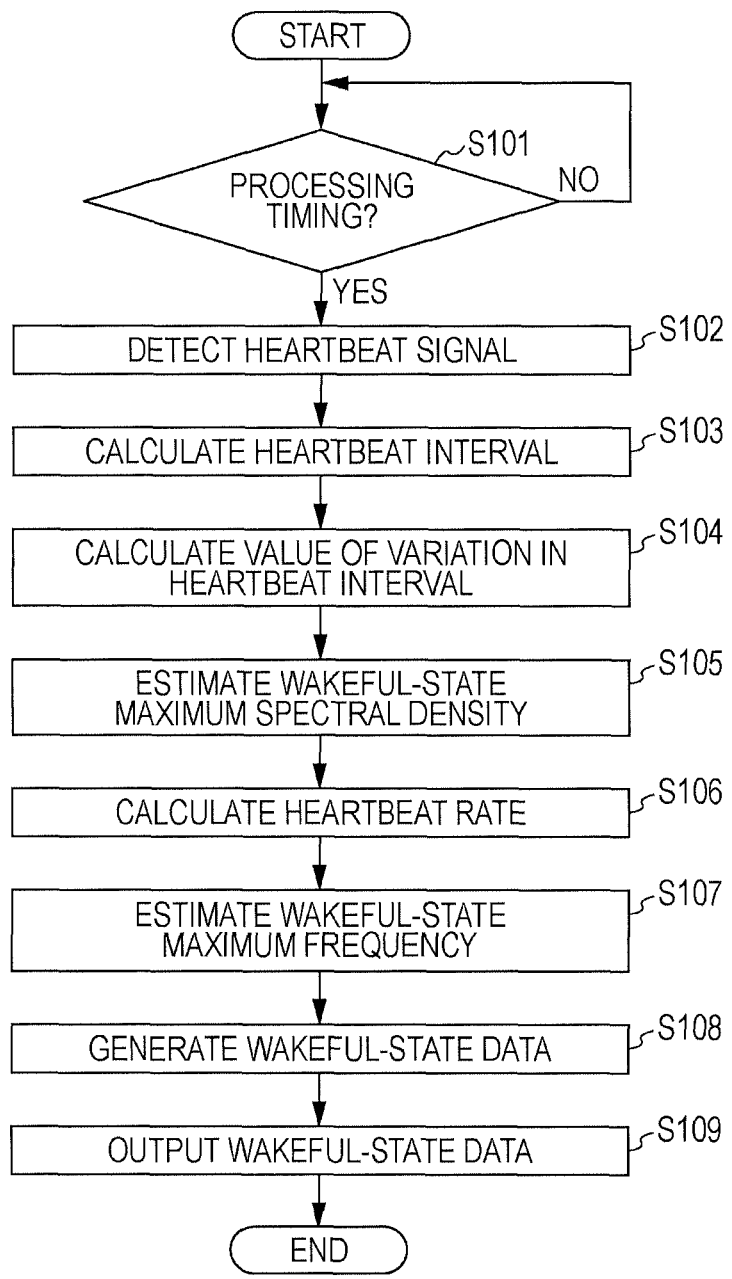
FIG. 12 is a flowchart illustrating the procedure of processing in the wakeful-state data generating apparatus according to Embodiment 1.

Next, the procedure of processing in the wakeful-state data generating apparatus 100 according to Embodiment 1 is described. FIG. 12 is a flowchart illustrating the procedure of processing in the wakeful-state data generating apparatus according to Embodiment 1. The processing illustrated in FIG. 12 is executed with acceptance of a processing start instruction from the user by the wakeful-state data generating apparatus 100 as a trigger, for example.

As illustrated in FIG. 12, when the processing timing arrives (process S101, Yes), the detecting unit 110 detects the heartbeat signal of the subject (process S102). The first calculating unit 120 calculates a heartbeat interval from the heartbeat signal of the subject (process S103). At this time, in order to create wakeful-state data, the detecting unit 110 acquires the heartbeat signal for about the duration of at least one respiration, and the first calculating unit 120 calculates a heartbeat interval from the heartbeat signal acquired by the detecting unit 110 for about the duration of at least one respiration. Further, the first calculating unit 120 calculates the value of variation in heartbeat interval (process S104).

The first estimating unit 130 estimates a wakeful-state maximum spectral density from the value of variation calculated by the first calculating unit 120 (process S105). For example, the first estimating unit 130 estimates a wakeful-state maximum spectral density from a wakeful-state RSA value, by using a correlation between wakeful-state RSA value and wakeful-state maximum spectral density.

The second calculating unit 140 calculates a heartbeat rate from the heartbeat signal of the subject (process S106). The second estimating unit 150 estimates a wakeful-state maximum frequency from the heartbeat rate calculated by the second calculating unit 140 (process S107). For example, the second estimating unit 150 calculates a wakeful-state respiration rate from a wakeful-state heartbeat rate, on the basis of a correlation between heartbeat rate and respiration rate. Then, by exploiting the fact that a respiratory period found from a respiration rate corresponds to a maximum frequency, the second estimating unit 150 calculates a wakeful-state maximum frequency from a wakeful-state respiration rate.

The generating unit 160 generates wakeful-state data including the wakeful-state maximum spectral density estimated in process S105, and the wakeful-state maximum frequency estimated in process S107 (process S108). The output unit 170 outputs the wakeful-state data generated by the generating unit 160 (process S109).

It should be noted that the procedure of processing described above may not necessarily be executed in the above-mentioned order. For example, the process of estimating a wakeful-state maximum spectral density may be executed after the process of estimating a wakeful-state maximum frequency is executed. That is, the order of processing may be such that processes S106 and S107 are executed after process S102 is executed, and then processes S103 to S105 are executed. Also, the process of estimating a wakeful-state maximum frequency and the process of estimating a wakeful-state maximum spectral density may be executed in parallel. That is, processes S106 and S107 and processes S103 to S105 may be executed in parallel after process S102 is executed.

Next, the effect of the wakeful-state data generating apparatus 100 according to Embodiment 1 is described. The wakeful-state data generating apparatus 100 calculates the value of variation in heartbeat interval from the heartbeat signal of the subject. The wakeful-state data generating apparatus 100 estimates the wakeful-state maximum spectral density of the subject from the calculated value of variation, on the basis of a pre-recorded correlation between value of variation and wakeful-state maximum spectral density. The wakeful-state data generating apparatus 100 calculates a heartbeat rate from the heartbeat signal. The wakeful-state data generating apparatus 100 estimates the wakeful-state maximum frequency of the subject from the calculated heartbeat rate, on the basis of a pre-recorded correlation between heartbeat rate and wakeful-state maximum frequency. The wakeful-state data generating apparatus 100 generates wakeful-state data including the estimated wakeful-state maximum spectral density and the estimated wakeful-state maximum frequency. In this way, the wakeful-state data generating apparatus 100 can easily generate wakeful-state data.

For example, the wakeful-state data generating apparatus 100 can generate wakeful-state data by using a heartbeat signal taken for several tens of seconds. Therefore, since the subject only needs to maintain a wakeful state for several tens of seconds when detecting a heartbeat signal, the wakeful-state data generating apparatus 100 can easily generate accurate wakeful-state data.

It should be noted that each of the following above-mentioned processing units: the first calculating unit 120, the first estimating unit 130, the second calculating unit 140, the second estimating unit 150, and the generating unit 160, corresponds to a device as described below, for example. That is, each of these processing units corresponds to an integrated device such as an application specific integrated circuit (ASIC) or a field programmable gate array (FPGA). Also, each of these processing units corresponds to an electronic circuit such as a central processing unit (CPU) or a micro processing unit (MPU).

Embodiment 2

Figure 13:
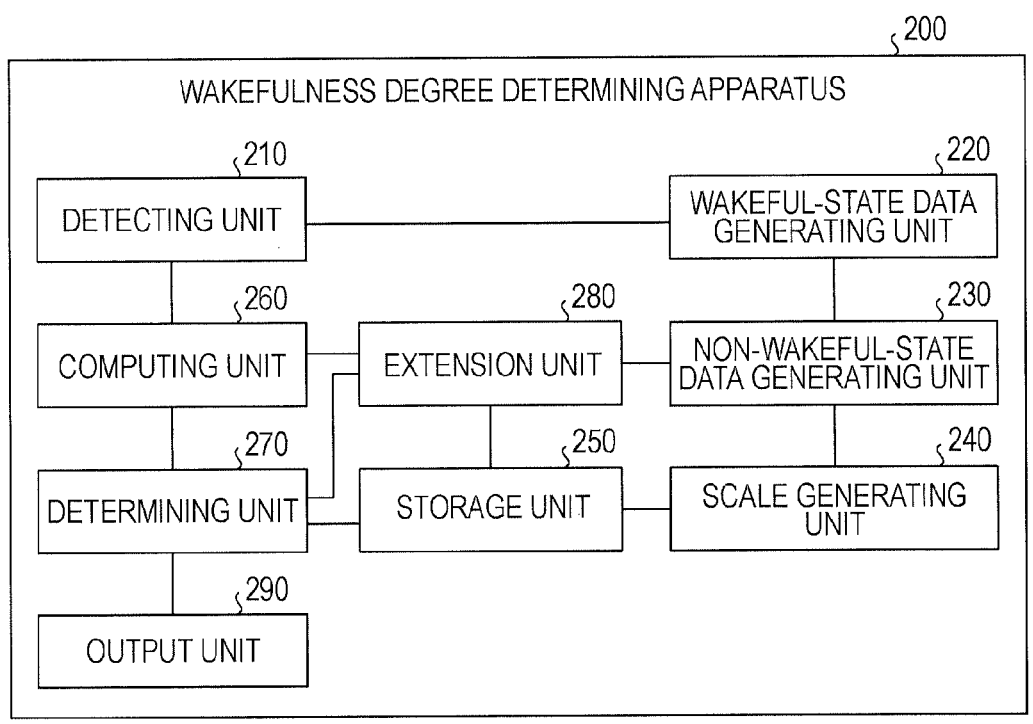
FIG. 13 is a diagram illustrating the functional configuration of a wakefulness degree determining apparatus according to Embodiment 2.

An example of the configuration of a wakefulness degree determining apparatus according to Embodiment 2 is described. FIG. 13 is a diagram illustrating the configuration of the wakefulness degree determining apparatus according to Embodiment 2. As illustrated in FIG. 13, a wakefulness degree determining apparatus 200 has a detecting unit 210, a wakeful-state data generating unit 220, a non-wakeful-state data generating unit 230, a scale generating unit 240, a storage unit 250, a computing unit 260, a determining unit 270, an extension unit 280, and an output unit 290.

The detecting unit 210 detects the heartbeat signal of the subject. For example, the detecting unit 210 applies voltage to electrodes in contact with the subject, and acquires the heartbeat signal of the subject from the potential difference between the electrodes. It should be noted that the subject corresponds to, for example, a driver who is driving a vehicle. Also, the electrodes used by the detecting unit 210 correspond to, for example, electrodes embedded in the steering wheel of the vehicle. Since the processing executed by the detecting unit 210 is the same as the processing executed by the detecting unit 110, a description of the detecting unit 210 is omitted.

The wakeful-state data generating unit 220 generates wakeful-state data in a case where no scale is set for the subject. For example, the wakeful-state data generating unit 220 calculates the value of variation in heartbeat interval from the heartbeat signal of the subject. The wakeful-state data generating unit 220 estimates the wakeful-state maximum spectral density of the subject from the calculated value of variation, on the basis of a pre-recorded correlation between value of variation and wakeful-state maximum spectral density. The wakeful-state data generating unit 220 calculates a heartbeat rate from the heartbeat signal. The wakeful-state data generating unit 220 estimates the wakeful-state maximum frequency of the subject from the calculated heartbeat rate, on the basis of a pre-recorded correlation between heartbeat rate and wakeful-state maximum frequency. The wakeful-state data generating unit 220 generates wakeful-state data including the estimated wakeful-state maximum spectral density and the estimated wakeful-state maximum frequency. It should be noted that the processing executed by the wakeful-state data generating unit 220 is the same as the processing executed by each of the first calculating unit 120, the first estimating unit 130, the second calculating unit 140, the second estimating unit 150, and the generating unit 160. Thus, a description of the wakeful-state data generating unit 220 is omitted. The wakeful-state data generating unit 220 corresponds to the wakeful-state data generating apparatus according to Embodiment 1.

The non-wakeful-state data generating unit 230 generates non-wakeful-state data including a non-wakeful-state maximum spectral density and a non-wakeful-state maximum frequency, on the basis of the wakeful-state data generated by the wakeful-state data generating unit 220. For example, the non-wakeful-state data generating unit 230 estimates the non-wakeful-state maximum spectral density of the subject from the wakeful-state maximum spectral density generated by the wakeful-state data generating unit 220, on the basis of a pre-recorded correlation between wakeful-state maximum spectral density and non-wakeful-state maximum spectral density. The non-wakeful-state data generating unit 230 estimates the non-wakeful-state maximum frequency of the subject from the wakeful-state maximum frequency generated by the wakeful-state data generating unit 220, on the basis of a pre-recorded correlation between wakeful-state maximum frequency and non-wakeful-state maximum frequency. The non-wakeful-state data generating unit 230 generates non-wakeful-state data including the estimated non-wakeful-state maximum spectral density and the estimated non-wakeful-state maximum frequency. It should be noted that the non-wakeful-state data generating unit 230 is an example of each of a third estimating unit, a fourth estimating unit, and a second generating unit.

Figure 14:
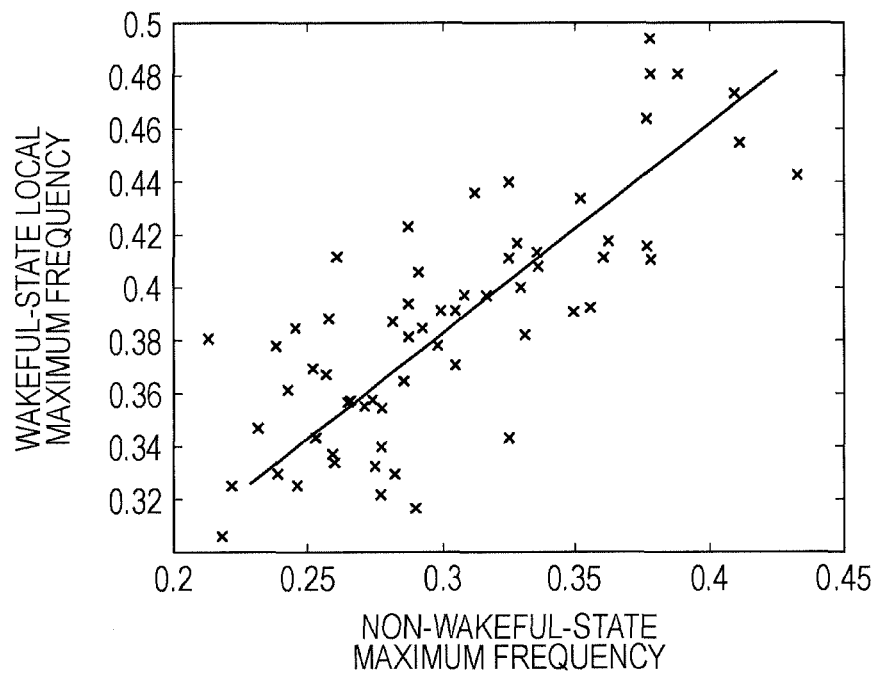
FIG. 14 is a diagram illustrating a correlation between wakeful-state maximum frequency and non-wakeful-state maximum frequency.
Figure 15:
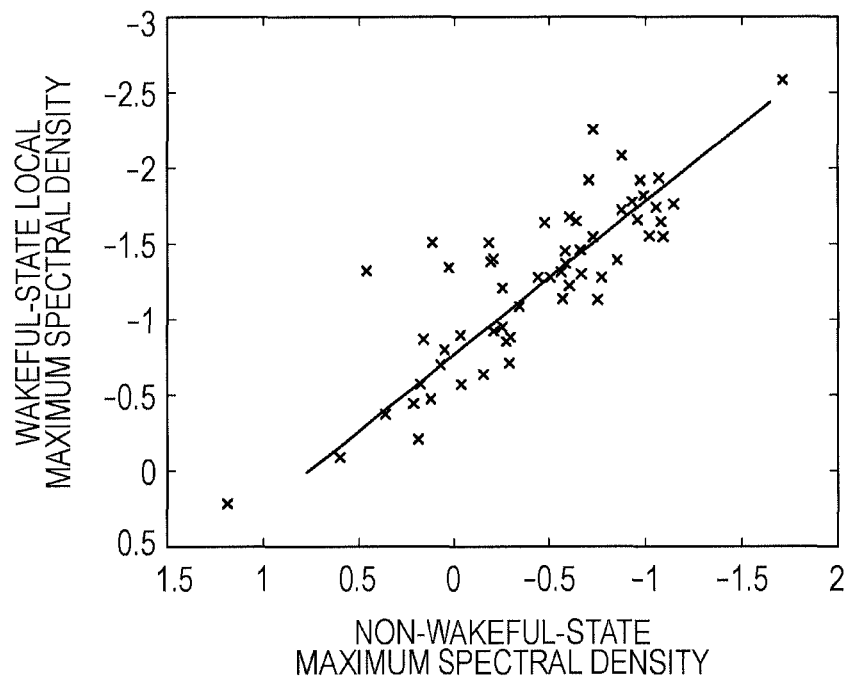
FIG. 15 is a diagram illustrating a correlation between wakeful-state maximum spectral density and non-wakeful-state maximum spectral density.

Now, the correlation used by the non-wakeful-state data generating unit 230 is described. FIG. 14 is a diagram illustrating a correlation between wakeful-state maximum frequency and non-wakeful-state maximum frequency. In FIG. 14, the horizontal axis represents non-wakeful-state maximum frequency, and the vertical axis represents wakeful-state maximum frequency. FIG. 15 is a diagram illustrating a correlation between wakeful-state maximum spectral density and non-wakeful-state maximum spectral density. In FIG. 15, the horizontal axis represents non-wakeful-state maximum spectral density, and the vertical axis represents wakeful-state maximum spectral density.

FIGS. 14 and 15 each illustrate an example of experimental results obtained by conducting an experiment in which the heartbeat signal of the subject was acquired using a driving simulator. As illustrated in FIGS. 14 and 15, by plotting values taken for individual subjects in a wakeful state and in a non-wakeful state, a regression line is obtained. The experimental results indicate that maximum frequency and maximum spectral density are correlated between a wakeful state and a non-wakeful state. It should be noted that in the example illustrated in FIGS. 14 and 15, the correlation factor for maximum frequency is 0.78, and the correlation factor for maximum spectral density is 0.85.

For example, the non-wakeful-state data generating unit 230 acquires wakeful-state data from the wakeful-state data generating unit 220. The non-wakeful-state data generating unit 230 substitutes the wakeful-state maximum frequency included in the acquired wakeful-state data, into the equation of the regression line illustrated in FIG. 14 to thereby calculate a non-wakeful-state maximum frequency. The non-wakeful-state data generating unit 230 substitutes the wakeful-state maximum spectral density included in the acquired wakeful-state data, into the equation of the regression line illustrated in FIG. 15 to thereby calculate a non-wakeful-state maximum spectral density. The non-wakeful-state data generating unit 230 generates the calculated non-wakeful-state maximum frequency and non-wakeful-state maximum spectral density as non-wakeful-state data. Then, the non-wakeful-state data generating unit 230 outputs the wakeful-state data and the non-wakeful-state data to the scale generating unit 240.

The description now returns to FIG. 13. The scale generating unit 240 generates an index of wakefulness degree by using the wakeful-state data generated by the wakeful-state data generating unit 220, and the non-wakeful-state data generated by the non-wakeful-state data generating unit 230. For example, as a scale serving as an index of wakefulness degree, the scale generating unit 240 generates the variable range of frequency and spectral density between the wakeful-state data and the non-wakeful-state data.

Figure 16:
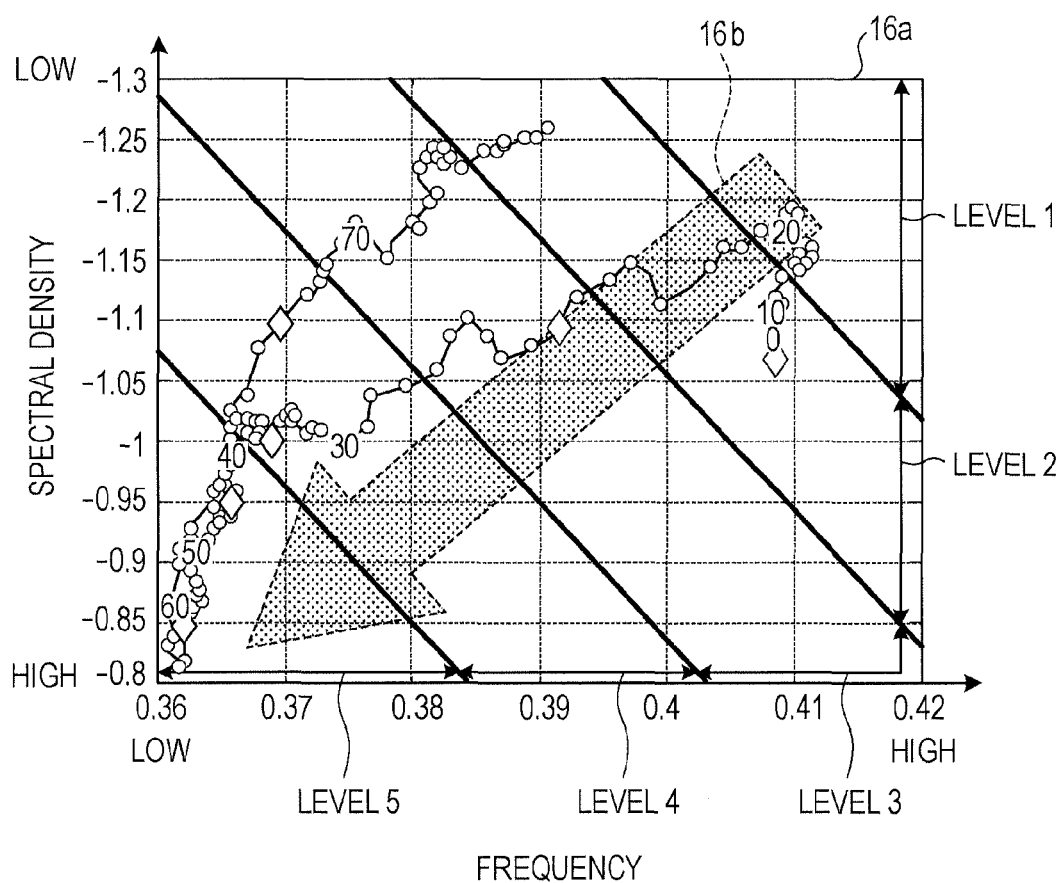
FIG. 16 is a diagram illustrating an example of scale.

Now, the scale set by the scale generating unit 240 is described. FIG. 16 is a diagram illustrating an example of scale. In FIG. 16, the horizontal axis represents frequency, and the vertical axis represents spectral density. In the example illustrated in FIG. 16, a scale 16a is set so that as indicated by a sleepiness direction 16b, sleepiness becomes weaker toward the upper right and sleepiness becomes stronger toward the lower left. In this case, the scale 16a is divided into five regions from the upper right toward the lower left, with five sleepiness levels assigned to the respective five regions. That is, the sleepiness level determined using the scale 16a is such that sleepiness increases and the degree of wakefulness decreases in order of Level 1 to Level 5. As illustrated in FIG. 16, the scale generating unit 240 retains the scale 16a that is normalized. The data of the scale set by the scale generating unit 240 includes, for example, an equation representing the boundary of each of the regions within the scale and the corresponding sleepiness level value. While FIG. 16 illustrates a case in which each of regions in the normalized scale 16a has an equal width, this should not be construed restrictively. For example, the width of each of regions in the normalized scale 16a may be adjusted so as to become narrower as the sleepiness level becomes higher. Also, the data of the scale is not limited to the structure described above, but may includes the frequency and spectral density of wakeful-state data, and the frequency and spectral density of non-wakeful-state data.

Figure 17:
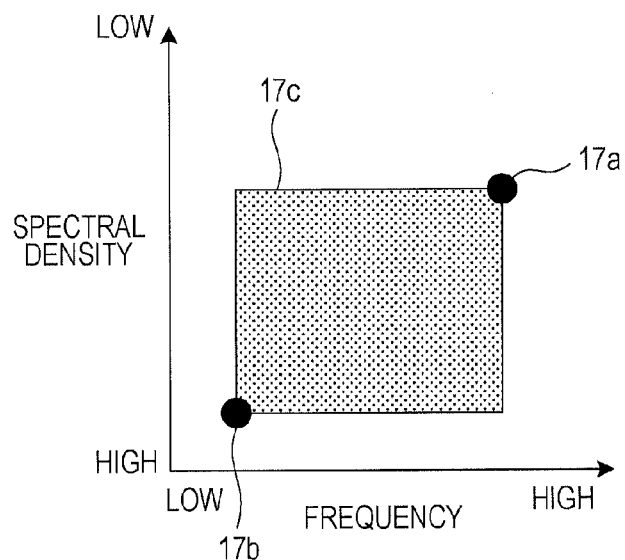
FIG. 17 is a diagram for explaining a process of generating a scale.

Subsequently, a process in which the scale generating unit 240 sets a scale is described. FIG. 17 is a diagram for explaining a process of generating a scale. In FIG. 17, the horizontal axis represents frequency, and the vertical axis represents spectral density. As illustrated in FIG. 17, the scale generating unit 240 generates a scale 17c by using wakeful-state data 17a and non-wakeful-state data 17b. For example, the scale generating unit 240 sets the largest value of frequency in the normalized scale 16a illustrated in FIG. 16 as corresponding to the maximum frequency of the wakeful-state data 17a. The scale generating unit 240 sets the smallest value of spectral density in the normalized scale 16a as corresponding to the maximum spectral density of the wakeful-state data 17a. The scale generating unit 240 sets the smallest value of frequency in the normalized scale 16a as corresponding to the maximum frequency of the non-wakeful-state data 17b. The scale generating unit 240 sets the largest value of spectral density in the normalized scale 16a as corresponding to the maximum spectral density of the non-wakeful-state data 17b. The scale generating unit 240 divides the scale 16a associated with the corresponding data into five equal parts, thereby setting individual regions corresponding to sleepiness levels. The scale generating unit 240 calculates an equation representing the boundary of each of the regions set in the scale 16a, thereby generating the scale 17c for the subject. Then, the scale generating unit 240 stores the generated scale 17c into the storage unit 250.

The description now returns to FIG. 13. The storage unit 250 stores the index of wakefulness degree generated by the scale generating unit 240. For example, the storage unit 250 stores the scale for the subject generated by the scale generating unit 240, in association with identification information for identifying the subject.

The computing unit 260 calculates a maximum frequency and a maximum spectral density from the heartbeat signal of the subject. For example, the computing unit 260 acquires a maximum point in spectral density data on the basis of heartbeat signal data inputted from the detecting unit 210, and calculates the maximum frequency and the maximum spectral density at the acquired maximum point.

Hereinbelow, processing executed by the computing unit 260 is described in detail. The computing unit 260 calculates a heartbeat interval from heartbeat signal data inputted from the detecting unit 210. The computing unit 260 generates heartbeat interval data indicating variation of heartbeat interval with elapse of time, on the basis of the calculated heartbeat interval. It should be noted that since the process in which the computing unit 260 calculates a heartbeat interval and the process in which the computing unit 260 calculates heartbeat interval data are the same as the processing executed by the first calculating unit 120, a description of these processes is omitted.

The computing unit 260 calculates spectral density for each frequency by performing frequency analysis on the heartbeat interval data. For example, the computing unit 260 calculates spectral density by using an auto regressive (AR) model. As disclosed in Sato Shunsuke, Kikkawa Sho, Kiryu Toru, "Introduction to bio-signal processing", CORONA publishing Co., Ltd., and the like, the AR model is a model that represents the state at a given point in time by the linear sum of past time-series data. The characteristic feature of the AR model is that clear maximum points can be obtained even with a small number of pieces of data as compared to Fourier transform.

An AR model of order p for time series x(s) is expressed by $$x(s) = \sum_{m=1}^{p} a(m)x(s-m) + e(s) \qquad (4)$$

Where a(m) is an AR coefficient that is a weight relative to a past value, and e(s) is an error term. Ideally, e(s) is white noise.

Letting p be degree of identification, $f_s$ be sampling frequency, $\epsilon_p$ be identification error, and $\hat{a}_p(k)$ be an AR coefficient of order k, spectral density $P_{AR}(f)$ is expressed by $$P_{AR}(f) = \frac{1}{f_s} \frac{\varepsilon_p}{\left|1 + \sum_{k=1}^{p} \hat{a}_p(k)e^{-2\pi jkf/f_s}\right|^2}. \qquad (5)$$

The computing unit 260 calculates spectral density on the basis of Equation (5) and the heartbeat interval data. It should be noted that the method of calculating spectral density is not limited to the above-described method. For example, the computing unit 260 may calculate spectral density by using Fourier transform.

The computing unit 260 generates spectral density data indicating spectral density for each frequency, upon each calculation of spectral density.

Figure 18:
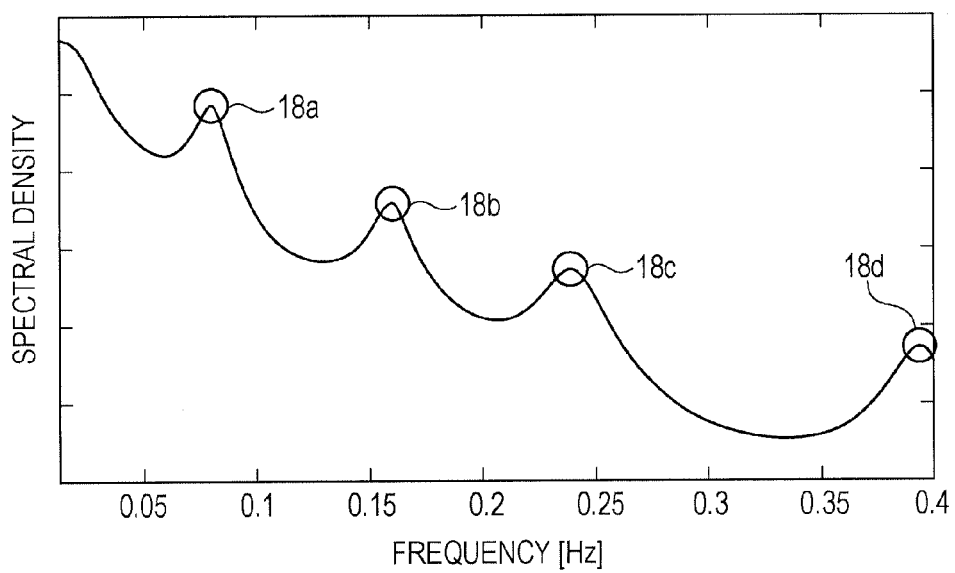
FIG. 18 is a diagram illustrating an example of spectral density data generated by a computing unit.

FIG. 18 is a diagram illustrating an example of spectral density data generated by the computing unit. In FIG. 18, the horizontal axis represents frequency, and the vertical axis represents spectral density. For example, a spectral density component appearing in a region in the vicinity of 0.05 to 0.15 Hz is a low frequency (LF) component reflecting the activated state of the sympathetic nervous system. Also, for example, a spectral density component appearing in a region in the vicinity of 0.15 to 0.4 Hz is a high frequency (HF) component reflecting the activated state of the parasympathetic nervous system.

The computing unit 260 acquires a maximum point at which spectral density in the spectral density data becomes maximum. For example, the computing unit 260 calculates frequency f that satisfies:

$$\frac{dP_{AR}(f)}{df} = 0 \quad (6)$$

as the frequency at a maximum point, and substitutes the frequency at this maximum point into Equation (5) to calculate the spectral density at the maximum point. In the example illustrated in FIG. 18, the computing unit 260 acquires four maximum points 18a, 18b, 18c, and 18d. It should be noted that the frequency at a maximum point is referred to as "maximum frequency", and the spectral density at a maximum point is referred to as "maximum spectral density".

The computing unit 260 selects one maximum point included in the HF component, from among the acquired maximum points 18a, 18b, 18c, and 18d. As illustrated in FIG. 18, if a plurality of maximum points are included in the HF component, the computing unit 260 selects the maximum point 18b with the lowest frequency. This is because the sleepiness of the subject can be determined more accurately by selecting a maximum point on the lower frequency side from among maximum points included in the HF component. If no maximum point is included in the HF component, the computing unit 260 selects one maximum point from the region on the side of frequencies higher than 0.4 Hz. Also, if one maximum point is included in the HF component, the computing unit 260 selects this maximum point.

The computing unit 260 calculates the maximum frequency and the maximum spectral density at the acquired maximum point. FIG. 19 is a diagram illustrating maximum frequency in a times series. In FIG. 19, the horizontal axis represents elapse of time, and the vertical axis represents frequency. FIG. 20 is a diagram illustrating maximum spectral density in a times series. In FIG. 20, the horizontal axis represents elapse of time, and the vertical axis represents spectral density. In a case where the computing unit 260 calculates spectral density data at intervals of 10 seconds, the interval between points in the time series direction illustrated in FIGS. 19 and 20 is 10 seconds. As illustrated in FIGS. 19 and 20, the computing unit 260 calculates a maximum frequency and a maximum spectral density every predetermined time period.

The description now returns to FIG. 13. The determining unit 270 determines the degree of the subject's wakefulness by comparing the maximum frequency and the maximum spectral density calculated by the computing unit 260, with the index of wakefulness degree generated by the scale generating unit 240. For example, the determining unit 270 accepts an input of identification information by the subject, and reads out a scale corresponding to the identification information from the storage unit 250. The determining unit 270 determines the degree of the subject's wakefulness by comparing the maximum point calculated by the computing unit 260 with the read-out scale. Specifically, for example, the determining unit 270 substitutes the maximum frequency and the maximum spectral density at the maximum point into the equation representing each region of the scale to thereby determine a region in which the calculated maximum point is included. The determining unit 270 determines the subject's sleepiness level in accordance with the region in which the maximum point is determined to be included. Then, the determining unit 270 outputs the determination results to the output unit 290. It should be noted that the method of accepting identification information is not limited to the method described above. For example, the determining unit 270 may use a method such as acquiring identification information from a camera image capturing the subject at the present time, or making a determination by using a region of the heartbeat signal which is characteristic of each individual person.

The extension unit 280 extends the index of wakefulness degree when the maximum frequency and the maximum spectral density calculated by the computing unit 260 lie outside a pre-set range of the index of wakefulness degree. For example, upon acquiring each of the maximum frequency and the maximum spectral density from the computing unit 260, the extension unit 280 determines whether or not the acquired value lies outside the scale for the subject stored in the storage unit 250.

If the acquired value lies off-scale, the extension unit 280 determines whether or not the distance between the acquired value and the scale is equal to or greater than a threshold. If the distance is not equal to or greater than the threshold, the extension unit 280 extends the scale for the subject, and stores the extended scale into the storage unit 250. On the other hand, if the distance is equal to or greater than the threshold, the extension unit 280 waits on standby until a maximum frequency and a maximum spectral density are acquired anew. It should be noted that the threshold used at this time is a value for eliminating errors at the time of heartbeat signal analysis. For example, the threshold is set to 0.1 with respect to the value of maximum frequency, so that if the value of maximum frequency deviates by 0.1 or more from the scale, it is determined that a different maximum point is being detected. The threshold is not limited to this example but may be set to an arbitrary value by a person using the wakefulness degree determining apparatus 200.

Figure 21A:
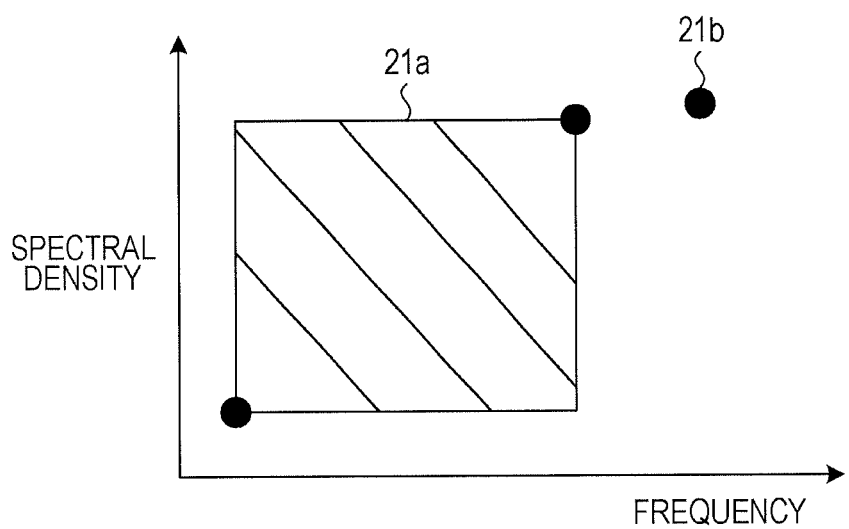
FIGS. 21A and 21B are diagrams for explaining a process of extending a scale entirely.
Figure 21B:
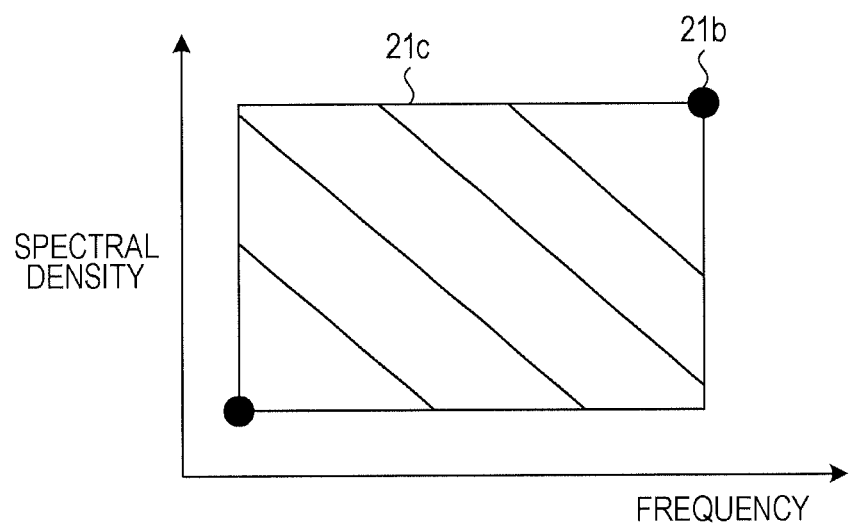

A process in which the extension unit 280 extends a scale is described. For example, the extension unit 280 moves each side of a pre-set scale so as to include an off-scale value. Then, the extension unit 280 sets a scale by applying a normalized scale to each side, thereby extending the scale entirely. FIGS. 21A and 21B are diagrams for explaining a process of extending a scale entirely. In FIGS. 21A and 21B, the horizontal axis represents frequency, and the vertical axis represents spectral density. As illustrated in FIGS. 21A and 21B, the extension unit 280 moves the upper side and right side of a scale 21a so that the scale 21a includes an off-scale value 21b. Then, the extension unit 280 sets a scale 21c by applying a normalized scale to each side, thereby extending the scale 21a entirely.

Figure 22:
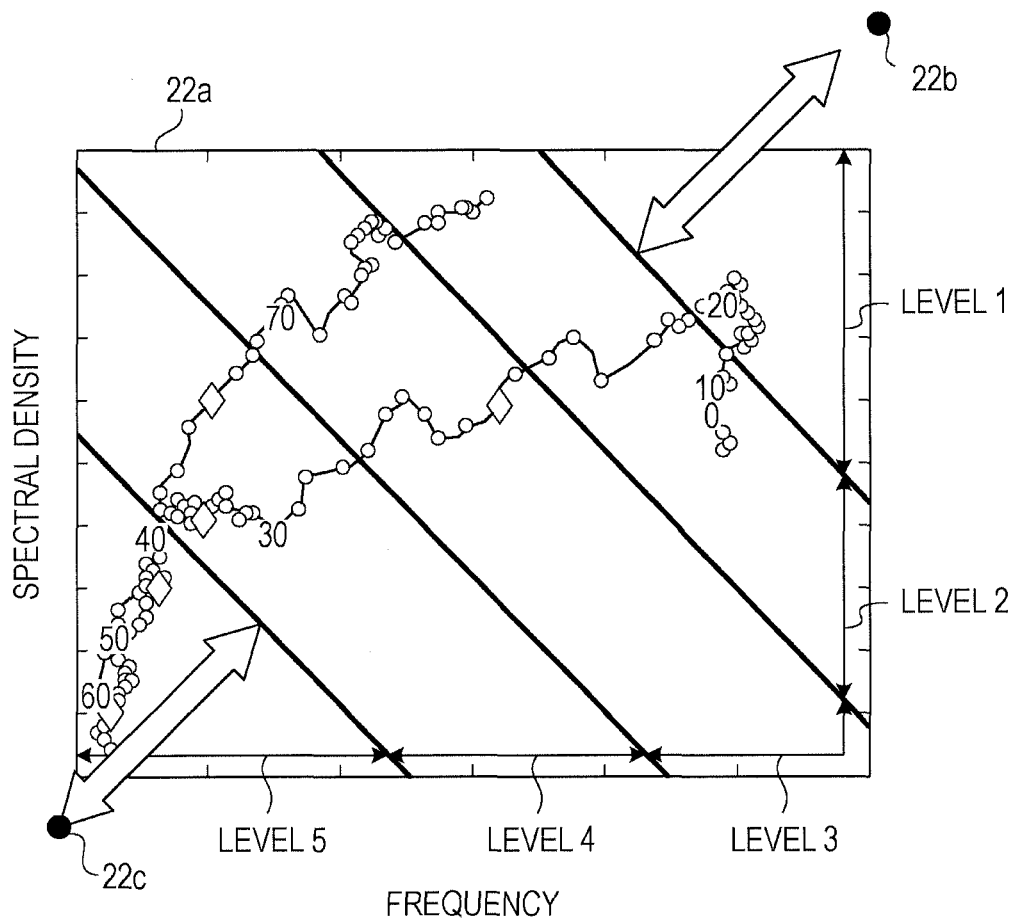
FIG. 22 is a diagram for explaining a process of extending a scale partially.

Also, for example, the extension unit 280 partially extends only a region of a pre-set scale which lies close to an off-scale value. FIG. 22 is a diagram for explaining a process of extending a scale partially. In FIG. 22, the horizontal axis represents frequency, and the vertical axis represents spectral density. As illustrated in FIG. 22, for example, when an off-scale value 22b lies to the upper right of a scale 22a, the extension unit 280 extends only the region of Level 1 with respect to the off-scale value 22b. Also, for example, when an off-scale value 22c lies to the lower left of the scale 22a, the extension unit 280 extends only the region of Level 5 with respect to the off-scale value 22c.

The reason why the extension unit 280 extends the scale is that when the maximum frequency and the maximum spectral density calculated by the computing unit 260 lie off-scale, the determining unit 270 is unable to determine the sleepiness level. For this reason, even when the calculated maximum frequency and maximum spectral density lie off-scale, the extension unit 280 extends the scale in order to determine the sleepiness level.

The output unit 290 outputs the determination results determined by the determining unit 270. The output unit 290 corresponds to, for example, a monitor or a speaker. For example, the output unit 290 notifies the subject, a nearby person around the subject, or the like of information indicating that the degree of the subject's wakefulness has decreased.

Figure 23:
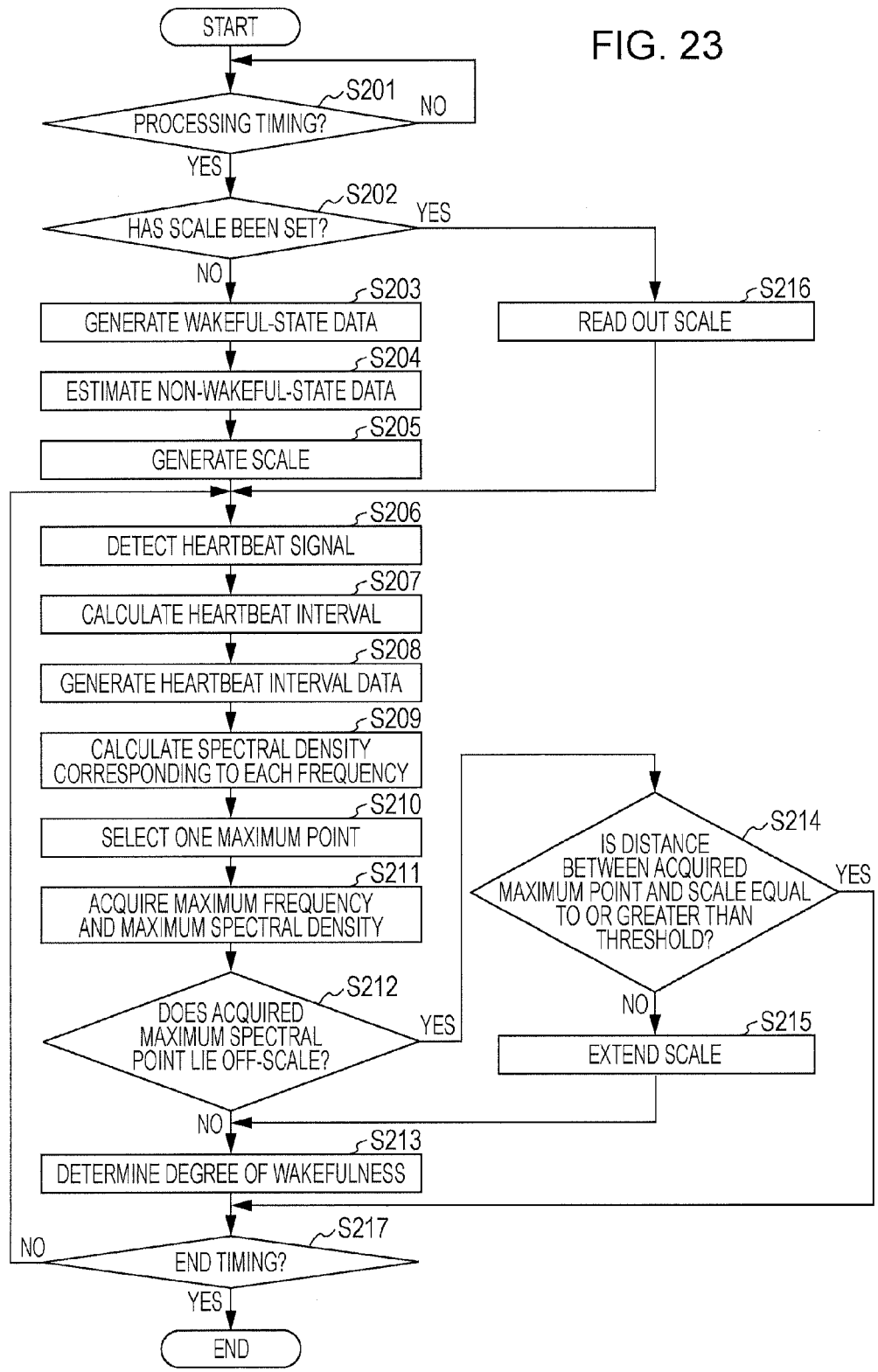
FIG. 23 is a flowchart illustrating the procedure of processing in the wakefulness degree determining apparatus according to Embodiment 2.

Next, the procedure of processing in the wakefulness degree determining apparatus 200 according to Embodiment 2 is described. FIG. 23 is a flowchart illustrating the procedure of processing in the wakefulness degree determining apparatus according to Embodiment 2. The processing illustrated in FIG. 23 is executed with activation of a vehicle system incorporating the wakefulness degree determining apparatus 200 as a trigger, for example.

As illustrated in FIG. 23, when the processing timing arrives (process S201, Yes), the wakeful-state data generating unit 220 determines whether or not a scale for the subject has been set (process S202). If a scale has not been set (process S202, No), the wakeful-state data generating unit 220 generates wakeful-state data (process S203). That is, the wakeful-state data generating unit 220 calculates the value of variation in heartbeat interval from the heartbeat signal of the subject. The wakeful-state data generating unit 220 estimates a wakeful-state maximum spectral density from the value of variation, on the basis of a correlation between the calculated value of variation and wakeful-state maximum spectral density. The wakeful-state data generating unit 220 calculates a heartbeat rate from the heartbeat signal, and estimates a wakeful-state maximum frequency on the basis of a correlation between the calculated heartbeat rate and wakeful-state maximum frequency. The wakeful-state data generating unit 220 generates wakeful-state data including the estimated wakeful-state maximum spectral density and the estimated wakeful-state maximum frequency. It should be noted that process S203 corresponds to processes S103 to S108 illustrated in FIG. 12.

The non-wakeful-state data generating unit 230 estimates non-wakeful-state data on the basis of the wakeful-state data generated by the wakeful-state data generating unit 220 (process S204). That is, the non-wakeful-state data generating unit 230 estimates a non-wakeful-state maximum spectral density from a wakeful-state maximum spectral density, on the basis of a correlation between the wakeful-state maximum spectral density estimated by the wakeful-state data generating unit 220 and non-wakeful-state maximum spectral density. The non-wakeful-state data generating unit 230 estimates a non-wakeful-state maximum frequency from a wakeful-state maximum frequency, on the basis of a correlation between the wakeful-state maximum frequency estimated by the wakeful-state data generating unit 220 and non-wakeful-state maximum frequency. The non-wakeful-state data generating unit 230 generates non-wakeful-state data including the estimated non-wakeful-state maximum spectral density and the estimated non-wakeful-state maximum frequency.

The scale generating unit 240 generates a scale by using the wakeful-state data and the non-wakeful-state data (process S205), and stores the generated scale into the storage unit 250.

The detecting unit 210 detects the heartbeat signal of the subject (process S206), and outputs heartbeat signal data to the computing unit 260. The computing unit 260 calculates a heartbeat interval from the heartbeat signal data inputted from the detecting unit 210 (process S207). The computing unit 260 generates heartbeat interval data indicating variation of heartbeat interval with elapse of time, on the basis of the calculated heartbeat interval (process S208).

The computing unit 260 calculates spectral density corresponding to each frequency by performing frequency analysis on the heartbeat interval data (process S209). The computing unit 260 selects one maximum point included in the HF component, from among maximum points at which spectral density becomes maximum (process S210). That is, upon each calculation of spectral density, the computing unit 260 generates spectral density data indicating spectral density for each frequency, and selects one maximum point included in the HF component, from among maximum points at which spectral density in the spectral density data becomes maximum.

The determining unit 270 acquires the maximum frequency and the maximum spectral density at the selected maximum point (process S211). That is, the determining unit 270 acquires the maximum point selected by the computing unit 260. If the acquired maximum point does not lie off-scale (process S212, No), the determining unit 270 determines the degree of the subject's wakefulness (process S213). That is, the determining unit 270 accepts an input of identification information by the subject, and reads out a scale corresponding to the identification information from the storage unit 250. The determining unit 270 determines the degree of the subject's wakefulness by comparing the maximum point calculated by the computing unit 260 with the read-out scale. Then, the output unit 290 outputs the determination results determined by the determining unit 270.

On the other hand, if the acquired maximum point lies off-scale (process S212, Yes), the extension unit 280 determines whether or not the distance between the acquired maximum point and the scale is equal to or greater than the threshold (process S214). If the distance is not equal to or greater than the threshold (process S214, No), the extension unit 280 extends the scale for the subject (process S215), and transfers to process S213.

On the other hand, if the distance is equal to or greater than the threshold (process S214, Yes), the extension unit 280 ends the scale extension process, and transfers to process S217.

On the other hand, if a scale for the subject has been set (process S202, Yes), the determining unit 270 accepts an input of identification information from the subject, reads out a scale corresponding to the identification information from the storage unit 250 (process S216), and transfers to process S206.

Until the end timing arrives (process S217, No), the wakefulness degree determining apparatus 200 repeats processes S206 to S217. Once the end timing arrives (process S217, Yes), the wakefulness degree determining apparatus 200 ends the processing. For example, the wakefulness degree determining apparatus 200 ends the processing in FIG. 23 with the end of the vehicle system incorporating the wakefulness degree determining apparatus 200 as a trigger.

Next, the effect of the wakefulness degree determining apparatus 200 according to Embodiment 2 is described. The wakefulness degree determining apparatus 200 calculates the value of variation in heartbeat interval from the heartbeat signal of the subject. The wakefulness degree determining apparatus 200 estimates a wakeful-state maximum spectral density from the value of variation, on the basis of a correlation between the calculated value of variation and wakeful-state maximum spectral density. The wakefulness degree determining apparatus 200 calculates a heartbeat rate from the heartbeat signal, and estimates a wakeful-state maximum frequency on the basis of a correlation between the calculated heartbeat rate and wakeful-state maximum frequency. The wakefulness degree determining apparatus 200 generates wakeful-state data including the estimated wakeful-state maximum spectral density and the estimated wakeful-state maximum frequency. The wakefulness degree determining apparatus 200 estimates a non-wakeful-state maximum spectral density, on the basis of a correlation between the estimated wakeful-state maximum spectral density and nonwakeful-state maximum spectral density. The wakefulness degree determining apparatus 200 estimates a non-wakeful-state maximum frequency, on the basis of a correlation between the estimated wakeful-state maximum frequency and non-wakeful-state maximum frequency. The wakefulness degree determining apparatus 200 generates non-wakeful-state data including the estimated non-wakeful-state maximum spectral density and the estimated non-wakeful-state maximum frequency. The wakefulness degree determining apparatus 200 generates an index of wakefulness degree by using the wakeful-state data and the non-wakeful-state data. Upon each detection of the heartbeat signal of the subject, the wakefulness degree determining apparatus 200 calculates a maximum frequency and a maximum spectral density from the heartbeat signal. The wakefulness degree determining apparatus 200 determines the degree of the subject's wakefulness, by comparing the calculated maximum frequency and maximum spectral density with the generated index of wakefulness degree. In this way, the wakefulness degree determining apparatus 200 can generate accurate wakeful-state data, and can easily generate an accurate scale. Therefore, the wakefulness degree determining apparatus 200 can accurately determine the degree of the subjects wakefulness.

It should be noted that each of the following above-mentioned processing units: the wakeful-state data generating unit 220, the non-wakeful-state data generating unit 230, the scale generating unit 240, the computing unit 260, the determining unit 270, and the extension unit 280, corresponds to a device as described below, for example. That is, each of these processing units corresponds to an integrated device such as an ASIC or FPGA. Also, each of these processing units corresponds to an electronic circuit such as a CPU or MPU.

Also, the storage unit 250 corresponds to, for example, a random access memory (RAM), a read only memory (ROM), a semiconductor memory device such as a flash memory, a hard disk, or an optical disc storage device.

Embodiment 3

While embodiments of the present invention have been described above, the present invention may be implemented in embodiments other than the above-mentioned embodiments. Accordingly, other embodiments are also described below.

For example, while Embodiment 1 described above is directed to the case in which the wakeful-state data generating apparatus 100 estimates a wakeful-state maximum frequency by using a heartbeat rate calculated from the heartbeat signal of the subject, the present invention is not limited to this. For example, the wakeful-state data generating apparatus 100 can accept an input of wakeful-state heartbeat rate from the subject, and estimates a wakeful-state maximum frequency by using the accepted heartbeat rate. For example, the second estimating unit 150 of the wakeful-state data generating apparatus 100 calculates a wakeful-state respiration rate by substituting the wakeful-state heartbeat rate accepted from the subject into Equation (2). Then, the second estimating unit 150 calculates a wakeful-state maximum frequency by substituting the calculated wakeful-state respiration rate into Equation (3).

Also, for example, while Embodiment 1 described above is directed to the case in which the wakeful-state data generating apparatus 100 estimates a wakeful-state maximum frequency by using the respiration rate of the subject, the present invention is not limited to this. For example, the wakeful-state data generating apparatus 100 can estimate a wakeful-state maximum frequency by using the basal metabolic rate of the subject [kcal/day]. This is because it is known that there is a correlation between respiration rate and basal metabolic rate. For example, the second estimating unit 150 of the wakeful-state data generating apparatus 100 calculates a wakeful-state maximum frequency F by using Equation (7) below.

$$F=0.15+(\text{basal metabolic rate})/C \tag{7}$$

It should be noted that "0.15" in Equation (7) represents the boundary frequency between the LF component reflecting the activated state of the sympathetic nervous system, and the HF component reflecting the activated state of the parasympathetic nervous system. Also, "C" denotes a constant that is set in advance on the basis of statistical data on a plurality of subjects. For example, "C" is obtained by executing a regression analysis using "C" as a response variable, and wakeful-state maximum frequency and basal metabolic rate as explanatory variables.

For example, the wakeful-state data generating apparatus 100 accepts information indicating sex and age from the subject, and acquires a basal metabolic rate on the basis of the accepted information. FIG. 24 is a diagram illustrating an example of a table describing basal metabolic rate by age. This table stores age, male basal metabolic rate, and female basal metabolic rate in association with each other. For example, the table stores age "18-29", male basal metabolic rate "1550", and female basal metabolic rate "1210" in association with each other. That is, the table indicates that the male basal metabolic rate for age 18-29 is 1550 [kcal/day], and the female basal metabolic rate for age 18-29 is 1210 [kcal/day]. For example, the wakeful-state data generating apparatus 100 acquires a basal metabolic rate on the basis of the table illustrated in FIG. 24, and substitutes the acquired basal metabolic rate into Equation (7) mentioned above to calculate the wakeful-state maximum frequency F. It should be noted that the method of acquiring a basal metabolic rate is not limited to the above-mentioned method using a table. For example, the wakeful-state data generating apparatus 100 may acquire a basal metabolic rate by using a relational expression for calculating a basal metabolic rate on the basis of the sex, age, height, and weight of the subject.

Figures 25, 26:
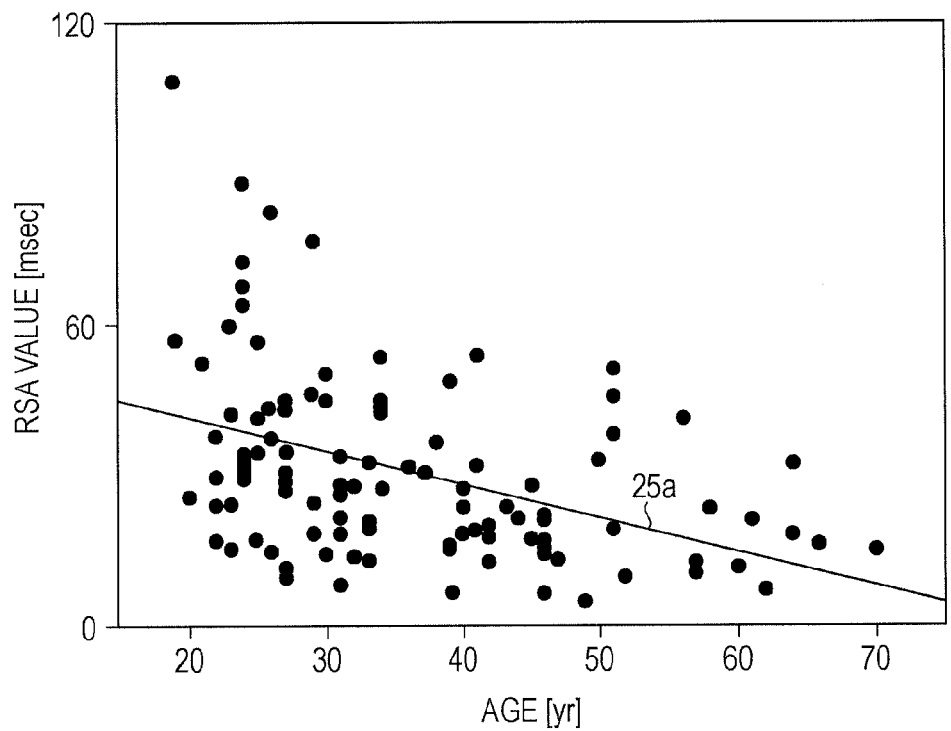
FIG. 25 is a diagram illustrating a correlation between age and RSA value.
FIG. 26 is a diagram illustrating an example of a table describing RSA value by age.

Also, for example, while Embodiment 1 described above is directed to the case in which the wakeful-state data generating apparatus 100 estimates a wakeful-state maximum spectral density by using the heartbeat signal of the subject, the present invention is not limited to this. For example, the wakeful-state data generating apparatus 100 can estimate a wakeful-state maximum spectral density by using the age of the subject. This is because it is known that there is a correlation between age and RSA value. FIG. 25 is a diagram illustrating a correlation between age and RSA value. In FIG. 25, the horizontal axis represents age [yr], and the vertical axis represents RSA value [msec]. As illustrated in FIG. 25, a regression line 25a is obtained by plotting age and wakeful-state RSA value for each of a plurality of subjects. For example, the wakeful-state data generating apparatus 100 substitutes the age of the subject into the equation of the regression line 25a to thereby calculate a wakeful-state RSA value. Then, the wakeful-state data generating apparatus 100 substitutes the wakeful-state RSA value into Equation (1) to thereby calculate a wakeful-state maximum spectral density. It should be noted that the method of calculating a wakeful-state RSA value from the age of the subject is not limited to the above-mentioned method. For example, the wakeful-state data generating apparatus 100 may find a wakeful-state RSA value from the age of the subject by using a table in which age and wakeful-state RSA value are associated with each other, as illustrated in FIG. 26. FIG. 26 is a diagram illustrating an example of a table describing RSA value by age.

Among the processes described with reference to Embodiments 1 and 2, all or part of the processes described as being performed automatically can be performed manually. Alternatively, all or part of the processes described as being performed manually can be performed automatically by known methods. For example, the series of processes in the wakefulness degree determining apparatus 200 illustrated in FIG. 23 may be executed with acceptance of an instruction from the driver as a trigger, after activation of the vehicle system incorporating the wakefulness degree determining apparatus 200.

Also, the processing procedures, control procedures, specific names, and information including various kinds of data and parameters described above or illustrated in the drawings can be changed in an arbitrary manner, unless otherwise specified. For example, the data of the scale generated by the scale generating unit 240 may include the frequency and spectral density of wakeful-state data, and the frequency and spectral density of non-wakeful-state data. In this case, since the values of wakeful-state data and non-wakeful-state data are stored in the storage unit 250, the determining unit 270 determines the sleepiness level after generating a scale again by applying a normalized scale to the values of wakeful-state data and non-wakeful-state data read out from the storage unit 250.

The respective components of the wakeful-state data generating apparatus 100 and wakefulness degree determining apparatus 200 in FIGS. 1 and 13 are illustrated functionally/conceptually, and may not necessarily be physically configured as illustrated in the drawings. That is, the specific forms of distribution/integration of the wakeful-state data generating apparatus 100 and wakefulness degree determining apparatus 200 are not limited to those illustrated in the drawings, and the whole or part of each apparatus may be configured so as to be functionally or physically distributed/integrated in arbitrary units in accordance with various loads, usage conditions, and so on. For example, the function of the wakeful-state data generating unit 220 illustrated in FIG. 13 may be included in an external device, and wakeful-state data generated in such an external device may be accepted by the wakefulness degree determining apparatus 200 to generate a scale.

Also, the wakeful-state data generating apparatus 100 and the wakefulness degree determining apparatus 200 can be implemented also by incorporating the respective functions of the wakeful-state data generating apparatus 100 and wakefulness degree determining apparatus 200 into a known information processing apparatus. The known information processing apparatus corresponds to, for example, an apparatus such as a personal computer, a work station, a portable telephone, a personal handy-phone system (PHS) terminal, a mobile communication terminal, or a personal digital assistant (PDA).

Figure 27:
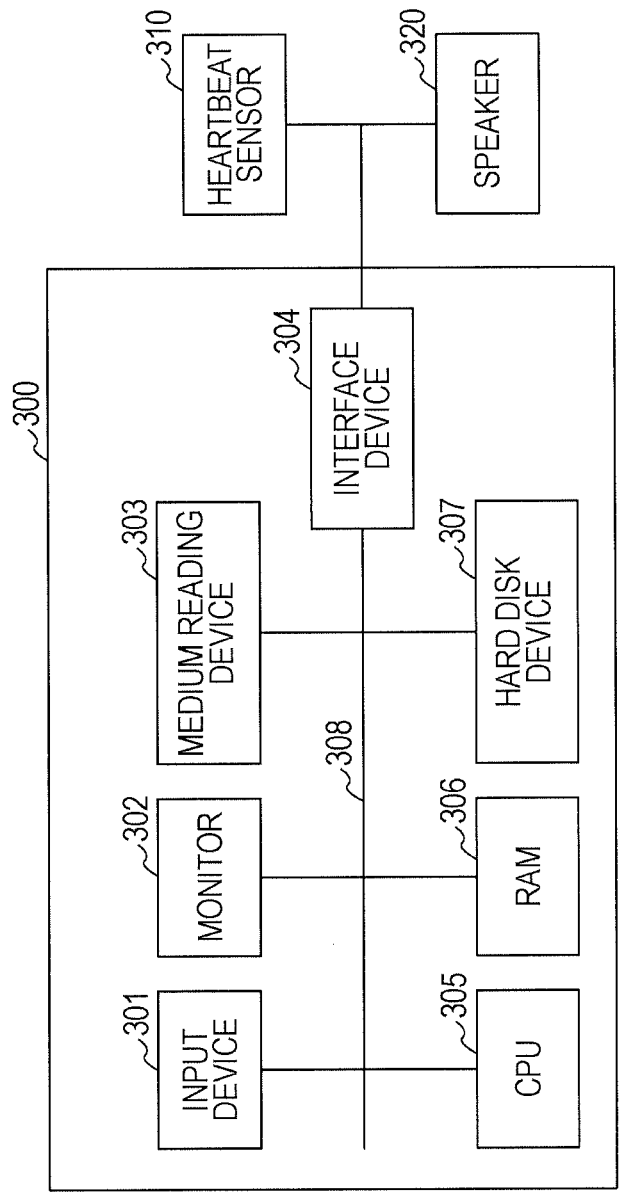
FIG. 27 is a diagram illustrating a computer that executes a wakeful-state data generating program according to Embodiment 1.

FIG. 27 is a diagram illustrating a computer that executes a wakeful-state data generating program according to Embodiment 1. As illustrated in FIG. 27, a computer 300 has an input device 301 that accepts an input of data from the user, a monitor 302, a medium reading device 303 that reads a program or the like from a storage medium, and an interface device 304 that exchanges data with another device. In addition, the computer 300 has a CPU 305 that executes various kinds of computational processing, a RAM 306 that temporarily stores various kinds of information, and a hard disk device 307. Each of the devices 301 to 307 is connected to a bus 308. The computer 300 is connected to a heartbeat sensor 310 that detects the heartbeat signal of the subject, and a speaker 320 via the interface device 304.

The hard disk device 307 stores various programs having functions similar to the following processing units illustrated in FIG. 1: the first calculating unit 120, the first estimating unit 130, the second calculating unit 140, the second estimating unit 150, and the generating unit 160. Also, the hard disk device 307 stores a scale for the subject in association with identification information for identifying the subject.

As various programs are read out from the hard disk device 307 and expanded and executed in the RAM 306 by the CPU 305, the various programs function as various processes. That is, the various programs function as processes similar to the following processing units: the first calculating unit 120, the first estimating unit 130, the second calculating unit 140, the second estimating unit 150, and the generating unit 160.

It should be noted that each of the various programs mentioned above may not necessarily be stored in the hard disk device 307. For example, a program stored in a computer-readable medium may be read out and executed by the computer 300. The computer-readable medium corresponds to, for example, a portable recording medium such as a CD-ROM, a DVD disc, or a USB memory, a semiconductor memory such as a flash memory, or a hard disk drive. Also, this program may be previously stored in a device connected to a public line, the Internet, a local area network (LAN), a wide area network (WAN), or the like, and the program may be read out from such a medium and executed by the computer 300. However, the computer-readable medium does not include a transitory medium such as a propagation signal. All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention(s) has(have) been described in detail, it should be understood that the various changes, substitutions, and alterations could be made hereto without departing from the spirit and scope of the invention.

What is claimed is:

1. A wakeful-state data generating apparatus comprising:
at least one processor and at least one storage device,
the at least one storage device configured to;
store a first correlation between value of variation in heartbeat interval and maximum spectral density, and
store a second correlation between heartbeat rate and wakeful-state maximum frequency,
the at least one processor configured to;
calculate a value of variation in heartbeat interval from a heartbeat signal of a subject,
estimate a wakeful-state maximum spectral density of the subject, on the basis of the first correlation and the calculated value of variation,
calculate a heartbeat rate from the heartbeat signal,
estimate a wakeful-state maximum frequency of the subject, on the basis of the second correlation and the calculated heartbeat rate, and
generate wakeful-state data including the estimated wakeful-state maximum spectral density and the estimated wakeful-state maximum frequency.

2. The wakeful-state data generating apparatus according to claim 1, wherein the at least one processor calculates respiratory sinus arrhythmia as the value of variation in heartbeat interval.

3. The wakeful-state data generating apparatus according to claim 1, wherein in estimating the wakeful-state maximum frequency, the at least one processor
  calculates a respiration rate of the subject on the basis of the calculated heartbeat rate, and
  estimates the wakeful-state maximum frequency on the basis of the respiration rate and the second correlation.

4. The wakeful-state data generating apparatus according to claim 1, further comprising:
  a detecting device that acquires the heartbeat signal of the subject,
  wherein the at least one processor acquires the heartbeat signal from the detecting device.

5. A wakeful-state data generating apparatus comprising:
  a first calculating unit that calculates a value of variation in heartbeat interval from a heartbeat signal of a subject;
  a first estimating unit that estimates a wakeful-state maximum spectral density of the subject from the value of variation calculated by the first calculating unit, on the basis of a pre-recorded correlation between value of variation and wakeful-state maximum spectral density;
  a second calculating unit that calculates a heartbeat rate from the heartbeat signal;
  a second estimating unit that estimates a wakeful-state maximum frequency of the subject from the heartbeat rate calculated by the second calculating unit, on the basis of a pre-recorded correlation between heartbeat rate and wakeful-state maximum frequency; and
  a generating unit that generates wakeful-state data including the wakeful-state maximum spectral density estimated by the first estimating unit, and the wakeful-state maximum frequency estimated by the second estimating unit.

6. The wakeful-state data generating apparatus according to claim 5, wherein the first calculating unit calculates respiratory sinus arrhythmia as the value of variation.

7. The wakeful-state data generating apparatus according to claim 5, wherein the second estimating unit
  calculates a respiration rate of the subject on the basis of the calculated heart rate, and
  estimates the wakeful-state maximum frequency on the basis of the respiration rate and the correlation between heartbeat rate and wakeful-state maximum frequency.

8. The wakeful-state data generating apparatus according to claim 5, further comprising a detecting unit that acquires the heartbeat signal of the subject.

9. A wakefulness degree determining apparatus comprising:
  at least one processor and at least one storage device,
  the at least one storage device configured to;
  store a first correlation between value of variation in heartbeat interval and maximum spectral density,
  store a second correlation between heartbeat rate and wakeful-state maximum frequency,
  store a third correlation between wakeful-state maximum spectral density and non-wakeful-state maximum spectral density, and
  store a fourth correlation between wakeful-state maximum frequency and non-wakeful-state maximum frequency, and
  the at least one processor configured to;
  calculate a value of variation in heartbeat interval from a heartbeat signal of a subject,
  estimate a wakeful-state maximum spectral density of the subject, on the basis of the first correlation and the calculated value of variation,
  calculate a heartbeat rate from the heartbeat signal,
  estimate a wakeful-state maximum frequency of the subject, on the basis of the second correlation and the calculated heartbeat rate,
  generate wakeful-state data including the wakeful-state maximum spectral density and the wakeful-state maximum frequency,
  estimate a non-wakeful-state maximum spectral density of the subject from the estimated wakeful-state maximum spectral density, on the basis of the third correlation,
  estimate a non-wakeful-state maximum frequency of the subject from the estimated wakeful-state maximum frequency, on the basis of the fourth correlation,
  generate non-wakeful-state data including the non-wakeful-state maximum spectral density and the non-wakeful-state maximum frequency, and
  generate an index of wakefulness degree related to determination of a degree of wakefulness, by using the wakeful-state data and the non-wakeful-state data.

10. The wakefulness degree determining apparatus according to claim 9, the at least one processor further configured to;
  calculate, upon each detection of a heartbeat signal of the subject, a new maximum frequency and a new maximum spectral density from the heartbeat signal, and
  determine a degree of wakefulness of the subject, by comparing the new maximum frequency and the new maximum spectral density with the index of wakefulness degree.

11. The wakefulness degree determining apparatus according to claim 10, wherein in determining the degree of wakefulness, the at least one processor determines that the lower the new maximum frequency and the higher the new maximum spectral density, the smaller the degree of wakefulness of the subject.

12. The wakefulness degree determining apparatus according to claim 9, wherein in generating the index, the at least one processor generates the index according to a magnitude of a value varying from the non-wakeful-state maximum spectral density to the wakeful-state maximum spectral density, and a magnitude of a value varying from the non-wakeful-state maximum frequency to the wakeful-state maximum frequency.

13. The wakefulness degree determining apparatus according to claim 9, wherein the at least one processor calculates respiratory sinus arrhythmia as the value of variation in heartbeat interval.

14. The wakefulness degree determining apparatus according to claim 9, wherein in estimating the wakeful-state maximum frequency, the at least one processor
  calculates a respiration rate of the subject on the basis of the calculated heartbeat rate, and
  estimates the wakeful-state maximum frequency on the basis of the respiration rate and the second correlation.

15. A wakefulness degree determining apparatus comprising:
  a first calculating unit that calculates a value of variation in heartbeat interval from a heartbeat signal of a subject;
  a first estimating unit that estimates a wakeful-state maximum spectral density of the subject from the value of variation calculated by the first calculating unit, on the basis of a pre-recorded correlation between value of variation and wakeful-state maximum spectral density;
  a second calculating unit that calculates a heartbeat rate from the heartbeat signal;
  a second estimating unit that estimates a wakeful-state maximum frequency of the subject from the heartbeat rate calculated by the second calculating unit, on the basis of a pre-recorded correlation between heartbeat rate and wakeful-state maximum frequency;

a first generating unit that generates wakeful-state data including the wakeful-state maximum spectral density estimated by the first estimating unit, and the wakeful-state maximum frequency estimated by the second estimating unit;

a third estimating unit that estimates a non-wakeful-state maximum spectral density of the subject from the wakeful-state maximum spectral density estimated by the first estimating unit, on the basis of a pre-recorded correlation between wakeful-state maximum spectral density and non-wakeful-state maximum spectral density;

a fourth estimating unit that estimates a non-wakeful-state maximum frequency of the subject from the wakeful-state maximum frequency estimated by the second estimating unit, on the basis of a pre-recorded correlation between wakeful-state maximum frequency and non-wakeful-state maximum frequency;

a second generating unit that generates non-wakeful-state data including the non-wakeful-state maximum spectral density estimated by the third estimating unit, and the non-wakeful-state maximum frequency estimated by the fourth estimating unit; and a scale generating unit that generates an index of wakefulness degree, by using the wakeful-state data generated by the first generating unit and the non-wakeful-state data generated by the second generating unit.

16. The wakefulness degree determining apparatus according to claim 15, further comprising:

a computing unit that calculates, upon each detection of a heartbeat signal of the subject, a new maximum frequency and a new maximum spectral density from the heartbeat signal; and a determining unit that determines a degree of wakefulness of the subject, by comparing the new maximum frequency and the new maximum spectral density with the index of wakefulness degree generated by the scale generating unit.

17. The wakefulness degree determining apparatus according to claim 16, wherein the determining unit determines that the lower the new maximum frequency and the higher the new maximum spectral density, the smaller the degree of wakefulness of the subject.

18. The wakefulness degree determining apparatus according to claim 15, wherein the scale generating unit generates the index according to a magnitude of a value ranging from the non-wakeful-state maximum spectral density to the wakeful-state maximum spectral density, and a magnitude of a value ranging from the non-wakeful-state maximum frequency to the wakeful-state maximum frequency.

19. The wakefulness degree determining apparatus according to claim 15, wherein the first calculating unit calculates respiratory sinus arrhythmia as the value of variation in heartbeat interval.

20. The wakefulness degree determining apparatus according to claim 15, wherein the second estimating unit
calculates a respiration rate of the subject on the basis of the calculated heartbeat rate, and
estimates the wakeful-state maximum frequency on the basis of the respiration rate and the correlation between heart rate and wakeful-state maximum frequency.

* * * * *